(12) United States Patent
Smith et al.

(10) Patent No.: US 10,932,670 B2
(45) Date of Patent: Mar. 2, 2021

(54) OPTICAL PRESSURE SENSOR ASSEMBLY

(71) Applicant: Avinger, Inc., Redwood City, CA (US)

(72) Inventors: Peter H. Smith, Pacifica, CA (US);
Manish Kankaria, Fremont, CA (US)

(73) Assignee: Avinger, Inc., Redwood City, CA (US)

( * ) Notice: Subject to any disclaimer, the term of this patent is extended or adjusted under 35 U.S.C. 154(b) by 821 days.

(21) Appl. No.: 14/776,748

(22) PCT Filed: Mar. 15, 2013

(86) PCT No.: PCT/US2013/032011
§ 371 (c)(1),
(2) Date: Sep. 15, 2015

(87) PCT Pub. No.: WO2014/142958
PCT Pub. Date: Sep. 18, 2014

(65) Prior Publication Data
US 2016/0038030 A1 Feb. 11, 2016

(51) Int. Cl.
*A61B 5/00* (2006.01)
*G01B 9/02* (2006.01)
(Continued)

(52) U.S. Cl.
CPC .......... *A61B 5/0084* (2013.01); *A61B 5/0066* (2013.01); *A61B 5/02154* (2013.01);
(Continued)

(58) Field of Classification Search
CPC ... A61B 5/00; A61B 2560/00; A61B 2562/00; A61B 2576/00; A61B 5/02154; G01B 9/00; G01L 9/00
See application file for complete search history.

(56) References Cited

U.S. PATENT DOCUMENTS 3,367,727 A   2/1968   Ward et al.
3,908,637 A   9/1975   Doroshow
(Continued)

FOREIGN PATENT DOCUMENTS

CN   1875242 A   12/2006
CN   1947652 A   4/2007
(Continued)

OTHER PUBLICATIONS

Shinkle et al.; Evaluation of stent placement and outcomes with optical coherence tomography; Interv. Cardiol.; 2(4); pp. 535-543; (manuscript version, 12 pages); Aug. 2010.
(Continued)

*Primary Examiner* — Pascal M Bui Pho
*Assistant Examiner* — Sean D Mattson
(74) *Attorney, Agent, or Firm* — Shay Glenn LLP

(57) ABSTRACT

Optical pressure sensor assemblies that can be used with existing catheters and imaging systems. Pressure sensors may be compatible with atherectomy and occlusion-crossing catheters, where intravascular pressure measurements at various vessel locations are needed to determine treatment efficacy. The pressure sensors may employ an optical pressure measurement mechanism using optical interferometry, and may be integrated with existing imaging modalities such as OCT. The pressure sensor assemblies may include a movable membrane that deflects in response to intravascular pressure; an optical fiber that transmits light to the movable membrane and receives light reflected or scattered back from the movable membrane into the fiber; and a processor or controller configured to determine the distance traveled by the light received in the fiber from the movable membrane, where the distance traveled is proportional to the intravascular pressure exerted against the membrane.

24 Claims, 23 Drawing Sheets

(51) Int. Cl.
*A61B 5/0215* (2006.01)
*G01L 9/00* (2006.01)

(52) U.S. Cl.
CPC .......... *A61B 5/6852* (2013.01); *A61B 5/7278* (2013.01); *G01B 9/02025* (2013.01); *G01B 9/02057* (2013.01); *G01B 9/02091* (2013.01); *A61B 2560/0238* (2013.01); *A61B 2560/0475* (2013.01); *A61B 2562/0233* (2013.01); *A61B 2562/0238* (2013.01); *A61B 2562/0247* (2013.01); *A61B 2576/00* (2013.01); *G01L 9/0077* (2013.01)

(56) References Cited

U.S. PATENT DOCUMENTS

| | | |
|---|---|---|
| 4,178,935 A | 12/1979 | Gekhaman et al. |
| 4,487,206 A * | 12/1984 | Aagard .............. A61B 5/02154 600/342 |
| 4,527,553 A | 7/1985 | Upsher |
| 4,552,554 A | 11/1985 | Gould et al. |
| 4,611,600 A * | 9/1986 | Cohen .................. A61B 5/0215 600/480 |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A * | 9/1987 | Kane .................. A61B 5/02154 600/480 |
| 4,771,774 A | 9/1988 | Simpson et al. |
| 4,841,977 A | 6/1989 | Griffith et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,018,529 A * | 5/1991 | Tenerz ............... A61B 5/02154 600/480 |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A * | 6/1995 | Chevalier .......... A61B 5/02154 600/488 |
| 5,429,136 A | 7/1995 | Milo et al. |
| 5,431,673 A | 7/1995 | Summers et al. |
| 5,437,284 A * | 8/1995 | Trimble ................ A61B 5/031 600/486 |
| 5,459,570 A | 10/1995 | Swanson et al. |
| 5,460,168 A | 10/1995 | Masubuchi et al. |
| 5,465,147 A | 11/1995 | Swanson |
| 5,507,795 A | 4/1996 | Chiang et al. |
| 5,517,998 A * | 5/1996 | Madison ............ A61B 5/02154 600/473 |
| 5,556,405 A | 9/1996 | Lary |
| 5,607,394 A | 3/1997 | Andersen et al. |
| 5,620,426 A | 4/1997 | Braithwaite |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,938,645 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A * | 11/1999 | Sawatari .............. A61B 5/0215 600/480 |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |

(56) References Cited

U.S. PATENT DOCUMENTS

| | | |
|---|---|---|
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Tang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,511 B2 | 5/2016 | Smith et al. |
| 9,351,757 B2 | 5/2016 | Kusleika |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |

(56) References Cited

U.S. PATENT DOCUMENTS

| | | |
|---|---|---|
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1* | 1/2006 | Chow-Shing ............ A61B 5/01 250/227.14 |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson et al. |
| 2010/0130996 A1 | 5/2010 | Doud et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0317973 A1 | 12/2010 | Nita |
| 2010/0324472 A1 | 12/2010 | Wulfman |
| 2011/0004107 A1 | 1/2011 | Rosenthal et al. |
| 2011/0023617 A1* | 2/2011 | Yu .................. G01L 9/0079 73/705 |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |

(56) References Cited

U.S. PATENT DOCUMENTS

| | | |
|---|---|---|
| 2012/0046679 A1 | 2/2012 | Patel et al. |
| 2012/0123352 A1 | 5/2012 | Fruland et al. |
| 2012/0238869 A1* | 9/2012 | Schmitt .............. A61B 5/0066 600/425 |
| 2012/0259337 A1 | 10/2012 | del Rio et al. |
| 2012/0289971 A1 | 11/2012 | Segermark et al. |
| 2013/0035692 A1 | 2/2013 | Sorensen et al. |
| 2013/0072787 A1 | 3/2013 | Wallace et al. |
| 2013/0096589 A1 | 4/2013 | Spencer et al. |
| 2013/0123615 A1 | 5/2013 | Spencer et al. |
| 2013/0138128 A1 | 5/2013 | Patel et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1* | 10/2013 | Higashi .............. A61B 5/02141 29/595 |
| 2013/0266259 A1 | 10/2013 | Bhagavatula et al. |
| 2013/0287282 A1 | 10/2013 | Yokota et al. |
| 2013/0289392 A1 | 10/2013 | Patel et al. |
| 2013/0296695 A1 | 11/2013 | Spencer et al. |
| 2013/0317519 A1 | 11/2013 | Romo et al. |
| 2013/0325003 A1 | 12/2013 | Kapur et al. |
| 2014/0005534 A1 | 1/2014 | He et al. |
| 2014/0128893 A1 | 5/2014 | Guggenheimer et al. |
| 2014/0187949 A1 | 7/2014 | Zhao et al. |
| 2014/0213893 A1 | 7/2014 | Simpson et al. |
| 2014/0222047 A1 | 8/2014 | Vreeman |
| 2014/0275996 A1 | 9/2014 | Stigall |
| 2014/0371718 A1 | 12/2014 | Alvarez et al. |
| 2015/0025310 A1 | 1/2015 | Everingham et al. |
| 2015/0099984 A1 | 4/2015 | Kankaria |
| 2015/0126856 A1 | 5/2015 | Tachibana et al. |
| 2015/0141816 A1 | 5/2015 | Gupta et al. |
| 2015/0164530 A1 | 6/2015 | Carver et al. |
| 2015/0208922 A1 | 7/2015 | Simpson et al. |
| 2015/0272615 A1 | 10/2015 | Newhauser et al. |
| 2015/0320975 A1 | 11/2015 | Simpson et al. |
| 2016/0192962 A1 | 7/2016 | Simpson et al. |
| 2016/0199092 A1 | 7/2016 | Patel et al. |
| 2018/0049700 A1 | 2/2018 | Black et al. |
| 2018/0256187 A1 | 9/2018 | Patel et al. |
| 2019/0021679 A1 | 1/2019 | Christensen |
| 2019/0021760 A1 | 1/2019 | Ketai et al. |

FOREIGN PATENT DOCUMENTS

| | | |
|---|---|---|
| CN | 101601581 A | 12/2009 |
| CN | 103027727 A | 4/2013 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2090245 A1 | 8/2009 |
| EP | 2353526 B1 | 9/2013 |
| JP | S62-275425 A | 11/1987 |
| JP | 03502060 A | 2/1990 |
| JP | 05103763 A | 4/1993 |
| JP | H06-027343 A | 2/1994 |
| JP | H07-308393 A | 11/1995 |
| JP | 2002-214127 A | 7/2002 |
| JP | 2004-509695 A | 4/2004 |
| JP | 2004-516073 | 6/2004 |
| JP | 2005-114473 A | 4/2005 |
| JP | 2005-249704 A | 9/2005 |
| JP | 2005230550 A | 9/2005 |
| JP | 2005-533533 A | 11/2005 |
| JP | 2008-175698 A | 7/2006 |
| JP | 2006-288775 A | 10/2006 |
| JP | 2006-313158 A | 11/2006 |
| JP | 2006-526790 | 11/2006 |
| JP | 2006-326157 A | 12/2006 |
| JP | 2007-83053 A | 4/2007 |
| JP | 2007-83057 A | 4/2007 |
| JP | 2007-225349 A | 9/2007 |
| JP | 2007533361 A | 11/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-66252 A | 4/2009 |
| JP | 2009-78150 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013/524930 A | 6/2013 |
| JP | 2016508758 A | 3/2016 |
| KR | 2007/0047221 | 5/2007 |
| RU | 2185859 C2 | 7/2002 |
| RU | 2218191 C2 | 12/2003 |
| WO | WO 91/17698 A1 | 11/1991 |
| WO | WO 99/23958 A1 | 5/1999 |
| WO | WO 00/54659 A1 | 9/2000 |
| WO | WO 01/15609 A1 | 3/2001 |
| WO | WO 01/76680 A1 | 10/2001 |
| WO | WO 2006/133030 A2 | 12/2006 |
| WO | WO2008/005888 A2 | 1/2008 |
| WO | WO 2008/029506 A | 3/2008 |
| WO | WO 2008/042987 A2 | 4/2008 |
| WO | WO2008/051951 A1 | 5/2008 |
| WO | WO 2008/065600 A2 | 6/2008 |
| WO | WO 2008/086613 A1 | 7/2008 |
| WO | WO 2008/087613 A2 | 7/2008 |
| WO | WO2009/005779 A1 | 1/2009 |
| WO | WO2009/006335 A1 | 1/2009 |
| WO | WO 2009/009799 A1 | 1/2009 |
| WO | WO2009/009802 A1 | 1/2009 |
| WO | WO 2009/023635 A | 2/2009 |
| WO | WO2009/024344 A1 | 2/2009 |
| WO | WO 2009/094341 A2 | 7/2009 |
| WO | WO 2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO 2011/044387 A2 | 4/2011 |
| WO | WO2011/062087 A1 | 5/2011 |
| WO | WO2012/057940 A1 | 5/2012 |
| WO | WO 2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |
| WO | WO2014/077870 A1 | 5/2014 |
| WO | WO2014/093148 A2 | 6/2014 |

OTHER PUBLICATIONS

Patel et al.; U.S. Appl. No. 15/324,325 entitled "High speed chronic total occulusion crossing devices," filed Jan. 6, 2017.

Kankaria; U.S. Appl. No. 15/419,815 entitled "Optical coherence tomography with graded index fiber for biological imaging," filed Jan. 30, 2017.

Simpson et al.; U.S. Appl. No. 15/434,758 entitled "Occlusion-crossing devices, imaging, and atherectomy devices," filed Feb. 16, 2017.

Simpson et al.; U.S. Appl. No. 15/457,960 entitled "Atherectomy catheters devices having multi-channel bushings," filed Mar. 13, 2017.

Patel et al.; U.S. Appl. No. 15/480,238 entitled "Guidewire positioning catheter," filed Apr. 5, 2017.

Smith et al.; U.S. Appl. No. 14/776,750 entitled "Chronic total occlusion crossing devices with imaging," filed Sep. 15, 2015.

Gupta et al.; U.S. Appl. No. 14/776,749 entitled "Tissue collection device for cathete," filed Sep. 15, 2015.

(56) References Cited

OTHER PUBLICATIONS

Aziz et al.; Chronic total occlusions—a stiff challenge requiring a major breakthrough: is there light at the end of the tunnel?; Heart; vol. 91; suppl. III; pp. 42-48; Jun. 2005.
Emkey et al.; Analysis and evaluation of graded-index fiber-lenses; Journal of Lightwave Technology; vol. LT-5; No. 9; pp. 1156-1164; Sep. 1987.
Gonzalo et al.; Optical coherence tomography patterns of stent restenosis; Am. Heart J.; 158(2); pp. 284-293; Aug. 2009.
Linares et al.; Arbitrary single-mode coupling by tapered and nontapered grin fiber lenses; Applied Optics; vol. 29; No. 28; pp. 4003-4007; Oct. 1, 1990.
Sharma et al.; Optical coherence tomography based on an all-fiber autocorrelator using probe-end reflection as reference; CWJ13; San Francisco, California; Cleo May 16, 2004; 4 pages.
Suparno et al.; Light scattering with single-mode fiber collimators; Applied Optics; vol. 33; No. 30; pp. 7200-7205; Oct. 20, 1994.
Han et al.; In situ Frog Retina Imaging Using Common-Path OCT with a Gold-Coated Bare Fiber Probe; CFM6; San Jose, California; Cleo, May 4, 2008; 2 pages.
Muller et al.; Time-gated infrared fourier-domain optical coherence tomography; CFM5; San Jose, California; Cleo May 4, 2008; 2 pages.
Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.
Wang et al.; Common-path endoscopic Fourier domain OCT with a reference Michelson interferometer; Proceedings of the SPIE; vol. 7566; pp. 75660L-75660L-7; Jan. 2010.
Rosenthal et al.; U.S. Appl. No. 15/354,898 entitled "Atherectomy catheter with laterally-displaceable tip," filed Nov. 17, 2017.
Patel et al.; U.S. Appl. No. 15/354,842 entitled "Atherectomy catheters and occlusion crossing devices," filed Nov. 17, 2016.
Smith et al.; U.S. Appl. No. 15/854,579 entitled "Chronic total occusion crossing devices with imaging," filed Dec. 26, 2017.
Patel et al.; U.S. Appl. No. 15/741,928 entitled "Micro-molded anamorpjic reflector lens for image guided therapeutic/diagnostic catheters," filed Jan. 4, 2018.
Zung et al.; U.S. Appl. No. 15/741,773 entitled "Self-alignment mechanism for imaging cather and drive assembly," filed Jan. 4, 2018.
Simpson et al.; U.S. Appl. No. 14/899,877 entitled "Occusion sheath for imaging catheter," filed Dec. 18, 2015.
Simpson et al.; U.S. Appl. No. 14/899,893 entitled "Identification of elastic lamina to guide interventional therapy," filed Dec. 18, 2015.
Patel et al.; U.S. Appl. No. 15/162,330 entitled "Atherectomy catheters with longitudinally displaceable drive shafts," filed May 23, 2016.
Spencer et al.; U.S. Appl. No. 15/162,353 entitled "Occlusion-crossing devices, atherectomy devices, and imaging," filed May 23, 2016.
Tachibana et al.; U.S. Appl. No. 15/162,391 entitled "Atherectomy catheter drive assemblies," filed May 23, 2016.
Rosenthal et al.; U.S. Appl. No. 16/105,743 entitled "Atherectomy catheter with laterally-displaceable tip," filed Aug. 20, 2018.
Patel et al.; U.S. Appl. No. 16/148,246 entitled "Atherectomy catheter with serrated cutter," filed Oct. 1, 2018.
Simpson et al.; U.S. Appl. No. 16/194,183 entitled "Indetification of elastic lamina to guide interventional therapy," filed Nov. 16, 2018.
Fernandez et al., U.S. Appl. No. 16/305,136 entitled "Catheter device with detachable distal end," filed Nov. 28, 2018.
Patel et al., U.S. Appl. No. 16/310,470 entitled "Atherectomy catheter with shapeable distal tip," filed Dec. 17, 2019.
Choma et al.; Sensitivity advantage of swept source and fourier domain optical coherence tomography; Optics Express; 11(18); pp. 2183-2189; Sep. 8, 2003.
De Boer et al.; Improved signal-to-noise ratio in spectral-domain compared with time-domain optical coherence tomography; Optics Letters; 28(21); pp. 2067-2069; Nov. 2003.
Leitgeb et al.; Performance of fourier domain vs time domain optical coherence tomography; Optics Express; 11(8); pp. 889-894; Apr. 21, 2003.
Rollins et al.; Optimal interferometer designs for optical coherence tomography; Optics Letters; 24(21); pp. 1484-1486; Nov. 1999.
Schmitt et al.; A new rotational thrombectomy catheter: System design and first clinical esperiences; Cardiovascular and Interventional Radiology; Sprinver-Verlag; 22(6); pp. 504-509; Nov. 1, 1999.
Tachibana et al.; U.S. Appl. No. 16/372,112 entitled "Atherectomy catheter drive assemblies," filed Apr. 1, 2019.
Radjabi et al.; U.S. Appl. No. 16/347,840 entitled "Methods, systems and apparatuses for displaying real-time catheter position," filed May 7, 2019.
Patel et al.; U.S. Appl. No. 16/490,903 entitled "Atherctomy catheter," filed Jul. 2, 2019.
Black et al; U.S. Appl. No. 16/506,851 entitled "Optical coherence tomography for biological imaging," filed Jul. 9, 2019.
Patel et al.; U.S. Appl. No. 16/516,093 entitled "High speed chronic total occlusion crossing devices," filed Jul. 18, 2019.
Stamper et al.; Plaque characterization with optical coherence tomography. Journal of the American College of Cardiology. 47(8); pp. 69-79; Apr. 18, 2006.
Patel et al.; U.S. Appl. No. 16/681,807 entitled "Atherectomy catheters and occlusion crossing devices," filed Nov. 12, 2019.
Bayer Material Science: ; Snap-Fit Joints for Plastics; 26 pages; retrieved from the Internet: ( https://web.archive.org/web/20121119232733if_/http://fab.cba.mit.edu:80/classes/S62.12/people/vemelle.noel/Plastic_Snap_fit_design.pdf) on Sep. 26, 2018.
Sharma et al.; Common-path optical coherence tomography with side-viewing bare fiber probe for endoscopic optical coherence tomography; vol. 78; 113102; 5 pages; Nov. 6, 2007.
Patel et al.; U.S. Appl. No. 16/801,047 entitled "Micro-molded anamorphic reflector lens for image guided therapeutic/diagnostic catheters," filed Feb. 25, 2020.

\* cited by examiner

OPTICAL PRESSURE SENSOR ASSEMBLY

CROSS REFERENCE TO RELATED APPLICATIONS

This patent application may be related to one or more of the following pending patent applications: U.S. application Ser. No. 12/790,703, entitled, "OPTICAL COHERENCE TOMOGRAPHY FOR BIOLOGICAL IMAGING," filed May 28, 2010; U.S. application Ser. No. 12/829,267, entitled, "CATHETER-BASED OFF-AXIS OPTICAL COHERENCE TOMOGRAPHY IMAGING SYSTEM," filed Jul. 1, 2010; International Application entitled, "OPTICAL COHERENCE TOMOGRAPHY WITH GRADED INDEX FIBER FOR BIOLOGICAL IMAGING" filed concurrently; U.S. application Ser. No. 13/433,049, entitled "OCCLUSION-CROSSING DEVICES, IMAGING, AND ATHERECTOMY DEVICES," filed Mar. 28, 2012; International Application entitled "OCCLUSION-CROSSING DEVICES" filed concurrently; International Application entitled," CHRONIC TOTAL OCCLUSION CROSSING DEVICES WITH IMAGING" filed concurrently; U.S. application Ser. No. 12/829,277, entitled, "ATHERECTOMY CATHETER WITH LATERALLY-DISPLACEABLE TIP," filed Jul. 1, 2010; U.S. application Ser. No. 13/175,232, entitled, "ATHERECTOMY CATHETERS WITH LONGITUDINALLY DISPLACEABLE DRIVE SHAFTS," filed Jul. 1, 2011; U.S. application Ser. No. 13/654,357, entitled, "ATHERECTOMY CATHETERS AND NON-CONTACT ACTUATION MECHANISM FOR CATHETERS," filed Oct. 17, 2012; U.S. application Ser. No. 13/675,867, entitled "OCCLUSION-CROSSING DEVICES, ATHERECTOMY DEVICES, AND IMAGING," filed Nov. 13, 2012; International Application entitled, "ATHERECTOMY CATHETERS WITH IMAGING" filed concurrently; International Application entitled, "BALLOON ATHERECTOMY CATHETERS WITH IMAGING" filed concurrently and International Application entitled, "ATHERECTOMY CATHETER DRIVE ASSEMBLIES" filed concurrently. Each of these patent applications is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Described herein are optical pressure sensing/sensor assemblies for measuring physiological parameters such as blood pressure and fractional flow reserve (FFR) in the peripheral and coronary vasculature. In particular, the optical pressure sensors and assembly use optical interferometry to calculate intravascular pressure. The described embodiments are compatible for use with existing imaging systems such as optical coherence tomography and can be used with atherectomy or other occlusion-crossing devices.

BACKGROUND

Assessing the pressure gradient across a portion of a patient's vasculature provides invaluable information regarding the existence of a stenotic lesion or other occlusion that necessitates surgical or other medical intervention. For example, peripheral artery disease (PAD) affects millions of people in the United States alone. PAD is a progressive narrowing of the blood vessels most often caused by atherosclerosis, the collection of plaque or a fatty substance along the inner lining of the artery wall. Over time, this substance hardens and thickens, which may interfere with blood circulation to the arms, legs, stomach and kidneys. This narrowing forms an occlusion, completely or partially restricting flow through the artery. Blood circulation to the brain and heart may be reduced, increasing the risk for stroke and heart disease. Similarly, coronary artery disease (CAD) is a narrowing or blocking of blood vessels that supply oxygen to the heart, which if left untreated can lead to severe life-threatening or painful conditions including angina pectoris, ischemic necrosis, or myocardial infraction.

Interventional treatments for PAD or CAD may include procedures for widening vessel lumens or clearing blockages. Endarterectomy is surgical removal of plaque from the blocked artery to restore or improve blood flow. Endovascular therapies such as atherectomy are typically minimally invasive techniques that open or widen arteries that have become narrowed or blocked. Other treatments may include angioplasty to open the artery. For example, a balloon angioplasty typically involves insertion of a catheter into a leg or arm artery and positioning the catheter such that the balloon resides within the blockage. The balloon, connected to the catheter, is expanded to open the artery. Surgeons may then place a wire mesh tube, called a stent, at the area of blockage to keep the artery open.

Although interventional treatments can be beneficial in managing and treating PAD or CAD, these treatments can also be completely ineffective where the occlusion is not severe enough to warrant intervention. Where a lesion is not large enough to substantially affect blood flow, atherectomies, stenting, or other occlusion removal treatments do not provide any overall benefit to the patient. Rather, employing these methods results in over-treating vessels without any commiserate improvement in the patient's condition.

One way to avoid over-treatment is to assess the pressure changes across an occlusion prior to treatment. If the pressure changes satisfy a threshold value, then the patient is a candidate for interventional procedures. Typically, referring to FIG. 1, pressure gradients across a portion of a vessel structure are determined by measuring a first pressure P1 at a first location on one side of a target treatment site and a second pressure P2 at a second location on the other end of the target treatment site. P1 and P2 are compared. In a healthy vessel, P1 and P2 should be approximately the same. However, in an obstructed or narrowed vessel, P1 is greater than P2 as the pressure increases as blood is forced to move through a narrowed cross-section.

Generally, P1 and P2 are compared by calculating a ratio relating the two. For example, in coronary vessels, the fractional flow ratio (FFR) may be calculated to assess whether a blockage is severe enough to actually limit blood flow to the heart. FFR is calculated by FFR=P1/P2. In some cases, the FFR calculation formula is shown, in the art, as Pd/Pa, where Pd is the pressure distal to the blockage (e.g. P1) and Pa is the pressure proximal to the blockage (P2). Regardless of the notation using distal or proximal, the concept is the same. The ratio compares the pressure at one location with another to determine the pressure differential across the target treatment section. A similar calculation can be used for any vessel to determine a pressure ratio.

Once the pressure gradient or ratio is determined, this value can be compared to an index indicating a threshold value at or above which interventional treatment is beneficial. For example, where the FFR is greater than 0.75, the blockage may be considered severe enough to limit blood flow and should be opened. In other cases, pressure ratios below a cut-off indicate that treatment is not warranted and would not significantly improve the patient's condition.

In addition to helping establish a course of treatment, pressure measurements during procedures also provide immediate feedback on efficacy. Pressure measurements may be taken during an atherectomy to determine whether the vessel has been widened enough to provide adequate blood flow through the lumen. This prevents over-cutting or excessive removal of tissue from the treatment site once pressure measurements reach a satisfactory range. Likewise, the pressure measurements provide feedback on the need for additional tissue excision where the pressure is still outside acceptable values.

Despite the advantages of having pressure readings, measuring intravascular pressure is challenging with available sensors. One reason for this is the dependence on electrical pressure sensors such as electrical pressure transducers. Electrical sensors operate by measuring electrical characteristics such as resistance or current flow induced by positive pressure acting on the sensor (e.g. movement of a sensor diaphragm to increase or decrease electrical resistance). A significant drawback of this type of sensor is calibration drift or electrical interference. The sensitivity of electrical sensors is susceptible to environmental disturbances such as changing temperature, which affect accuracy. Accordingly, there is a need for an optical pressure sensor that avoids these electrical interferences such as drift.

An additional challenge has been the ease of using pressure sensors with existing atherectomy, occlusion-crossing devices, or vessel imaging systems (e.g. optical coherence tomography). Because these devices are designed to be introduced into and advanced through a patient's narrow vasculature, it is often challenging to include additional components for a pressure sensor without detracting from the optimal size of the devices. Moreover, the mechanisms of pressure measurement for existing sensors are often independent or incompatible with imaging modalities (e.g. OCT) utilized on devices. As such, there is a need for an optical pressure sensor that is easily integrated or incorporated into existing vascular treatment devices.

Embodiments described herein address at least these concerns. In particular, contemplated embodiments provide for optical pressure sensors and sensor assemblies that can be used alone or in conjunction with existing PAD or CAD treatment systems.

SUMMARY OF THE DISCLOSURE

The present invention relates to optical pressure sensing devices, systems, and methods.

Some embodiments described herein provide for an optical pressure sensor assembly, having an optical fiber; a housing having a first end and a second end, the housing including a lumen through which the optical fiber extends, the housing having an opening at the first end; an elastic membrane attached to the housing and positioned at the opening, the elastic membrane configured to be movable relative to the housing in response to pressure; and an optical fiber connector attached to a proximal end of the fiber, the connector configured for optical communication with a light source.

In some embodiments, a distal end of the optical fiber is secured in the housing near the opening, the distal end of the fiber may be configured to transmit light from a light source to the elastic membrane and to receive light reflected or scattered by the elastic membrane. In additional embodiments, the optical fiber is moveable relative to the housing.

In any of the preceding embodiments, the elastic membrane is adapted to deflect toward the optical fiber under positive pressure. In some of the embodiments, the elastic membrane includes a convex surface facing the optical fiber when the membrane is deflected under positive pressure. In any of the preceding embodiments, the elastic membrane is configured to cover the opening.

In any of the preceding embodiments, the elastic membrane is adapted to reflect and scatter light toward a distal end of the optical fiber. In any of the preceding embodiments, the elastic membrane is made from fluorinated ethylene propylene.

In any of the preceding embodiments, the elastic membrane includes a first surface facing the optical fiber and a second surface facing an intravascular lumen, the distance between the first surface and the optical fiber decreasing when positive pressure is applied to the second surface of the elastic membrane. In any of the preceding embodiments, the elastic membrane is adapted to move toward a central longitudinal axis of the housing under positive pressure.

In any of the preceding embodiments, the pressure sensor device or assembly includes a memory storage device storing pressure sensor calibration data. The storage device may be an EEPROM storing pressure sensor calibration data for the assembly. In any of the preceding embodiments, the calibration data includes a pressure to deflection relationship for the elastic membrane. In any of the preceding embodiments, the pressure sensor device or assembly includes a mirror aligned with the opening to reflect light exiting the fiber toward the elastic membrane.

Any of the preceding embodiments may include an interface medium at the distal end of the optical fiber, the interface medium having a first refractive index different from a second refractive index of the optical fiber, wherein the differing refractive indices creates a Fresnel reflection. In some embodiments, the interface medium is an adhesive such as Masterbond EP42HT-2, EpoTek OG127-4 or OG116, or UV curable photonics adhesive OP-4-20658.

Any of the preceding embodiments may include a rotational mechanism configured to rotate a portion of the assembly to generate an OCT image.

In any of the preceding embodiments, a catheter may form the housing and the catheter may have an outer diameter of about 0.14 inches to about 0.19 inches. In any of the preceding embodiments, a catheter may form the housing and the catheter may have an outer diameter of about 0.014 inches to about 0.019 inches.

In any of the preceding embodiments, the optical connector includes a lens configured to transmit collimated light into a proximal end of the fiber.

In any of the preceding embodiments, the assembly is dimensioned for insertion through a catheter lumen.

Other embodiments provide for an optical pressure sensor system for sensing intravascular blood pressure including a pressure wire assembly having an elongate hollow body having a proximal end and a distal end, a tip portion located at the distal end; an opening on the tip portion formed through a wall of the elongate hollow body; an optical fiber extending through the elongate body, the fiber having a light emitting distal end and a proximal end having an optical connector; and a flexible membrane at the opening, the membrane adapted to move under pressure; and an optical imaging system having a controller, a light source, and a detector, the light source in optical communication with the fiber and the detector configured to receive light reflected or scattered by the membrane. In any of the preceding embodiments, the pressure wire assembly is adapted to measure a pressure exerted on an outer surface of the membrane. In any of the preceding embodiments, the pressure wire assembly is configured to generate a Fresnel reference light.

In any of the preceding embodiments, the controller may be configured to operate the detector and control the transmission of light from the light source. In some variations, the controller is in electrical communication with an optical switch, the optical switch configured to move between at least two modes, one of the modes providing optical communication from the light source through the optical switch and into the optical connector on the proximal end of the fiber. In some cases, the controller is configured to generate a pressure value for the pressure exerted on the outer surface of the membrane, the pressure value generated based on the movement of the flexible membrane in response to the pressure exerted on the outer surface the membrane.

In any of the preceding embodiments, the detector receives an interference signal resulting from the interaction of the Fresnel reference light and light reflected or scattered by membrane. In any of the preceding embodiments, the controller receives the interference signal from the detector and computes a pressure measurement based on the interference signal. In any of the preceding embodiments, the controller receives the interference signal from the detector and computes a pressure measurement based on the interference signal and a deflection-to-pressure relationship for the membrane. In any of the preceding embodiments, the controller computes a pressure value based on a distance between the fiber distal end and the membrane.

Any of the preceding embodiments may include an intravascular catheter device having a hollow shaft adapted for insertion into a blood vessel, the pressure wire assembly dimensioned for insertion through the hollow shaft. In some embodiments, the pressure wire assembly has an outer diameter between about 0.014 inches to about 0.019 inches. In some embodiments, the pressure wire assembly has an outer diameter between about 0.14 inches to about 0.19 inches.

In any of the preceding embodiments, the pressure wire assembly includes an interface medium at the distal end of the fiber, the interface medium having a first refractive index different from a second refractive index of a fiber core in the optical fiber.

Other embodiments provide a pressure measurement system having an optical radiation source; a pressure probe, the probe having an optical fiber; a housing surrounding a portion of the optical fiber, a distal end of the fiber positioned at an opening of the housing at a first end of the housing; a resilient sheath overlaid across the opening in the housing, the sheath adapted to deflect in response to a pressure exerted on an outer surface of the sheath, the optical fiber configured to transmit optical radiation to the sheath and receive optical radiation reflected or scattered by the sheath while the sheath is deflected; and an optical connector in optical communication with an optical radiation source. The pressure measurement system may include receiving electronics to receive reflected or scattered optical radiation from the optical fiber and a processor configured to compute a pressure value based upon the optical radiation received by the receiving electronics.

Any of the preceding embodiments may include a display in communication with the processor, the display configured for displaying measured pressure values.

In any of the preceding embodiments, the resilient sheath is a flexible membrane adapted to deflect toward the optical fiber under positive pressure from the environment. In any of the preceding embodiments, the optical fiber is removable from the housing.

In any of the preceding embodiments, the resilient sheath is a flexible membrane having a convex surface facing the optical fiber when deflected by pressure exerted on the outer surface.

In any of the preceding embodiments, the processor is configured to generate the pressure value by comparing the optical radiation received by the receiving electronics with a set of pressure calibration data for the probe.

Any of the preceding embodiments may include a memory storage device in which the set of calibration data is stored. The memory storage device may be an EEPROM. In any of the preceding embodiments, the calibration data comprises a pressure-deflection relationship for the resilient sheath.

Any of the preceding embodiments may include a catheter forming the housing. In some embodiments, the optical fiber is adhered to the housing.

Any of the preceding embodiments may include a rotational mechanism configured to rotate the probe to generate an OCT image. Any of the preceding embodiments may include a mirror near the opening, the mirror configured to reflect optical radiation from the fiber to the sheath.

In any of the preceding embodiments, the optical fiber comprises a core providing a common path for optical radiation reflected from a reference and the sheath.

In any of the preceding embodiments, the receiving electronics includes a detector.

Further embodiments provide for methods of determining pressure in a blood vessel. These methods include transmitting light from a source through an optical fiber; transmitting the light from the optical fiber to a deflected surface of an elastic membrane, wherein the elastic membrane is moveable in response to pressure exerted against the membrane; transmitting reflected or scattered light from the elastic membrane to a detector; receiving the reflected or scattered light at the detector; generating a intravascular pressure measurement from the light received by the detector from the elastic membrane.

In any of the preceding embodiments, the generating step includes computing the pressure measurement based on a membrane deflection distance between the membrane surface and the optical fiber. In any of the preceding embodiments, the deflection distance is indicated by an intensity value and a pixel depth value for the light received by the detector from the elastic membrane.

In any of the preceding embodiments, the generating step includes transmitting data from the detector to a processor, wherein the data represents an interference signal resulting from the interaction of a reference reflected light and a membrane scattered or reflected light, the processor computing an intravascular pressure based on the interference signal.

In any of the preceding embodiments, the generating step includes computing a path length from the optical fiber and the deflected surface of the membrane, the computation based on a difference in phase, time or frequency between a reference reflected light and a membrane scattered or reflected light.

Any of the preceding embodiments may include calculating a fractional flow reserve for the vessel. Any of the preceding embodiments may include calculating a first pressure at a first location and a second pressure at a second location.

Further embodiments provide for methods of determining pressure in a vessel with an OCT catheter. These methods include advancing an optical fiber through a lumen of the catheter; transmitting light from a source through an optical fiber; transmitting the light from the optical fiber to a flexible elastic membrane on the catheter, wherein the elastic membrane deflects toward the fiber under pressure; transmitting reflected or scattered light from the elastic membrane to a detector; receiving the reflected or scattered light at the detector; generating an intravascular pressure measurement based on the light received by the detector from the elastic membrane.

Any of the preceding embodiments may include computing the pressure measurement based on a membrane deflection distance. Any of the preceding embodiments may include generating an OCT image by rotating a portion of the catheter.

Further embodiments describe an OCT pressure sensing device including an elongate body; a central lumen extending within the elongate body from a proximal end of the elongate body to a distal end of the elongate body; a rotatable tip at the distal end of the elongate body and configured to rotate relative to the elongate body, the rotatable tip having an open across which sits an elastic membrane, the membrane adapted to deflect in response to a pressure exerted against an outer surface of the membrane; and an optical fiber coupled with the rotatable tip and configured to rotate therewith.

In any of the preceding embodiments, the optical fiber is an OCT imaging sensor. In any of the preceding embodiments, the optical fiber and elastic membrane are adapted to measure pressure exerted against the device. In any of the preceding embodiments, the optical fiber and elastic membrane measure pressure while the rotational position of the device is relatively fixed.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Embodiments described herein provide for optical pressure sensor assemblies that utilize the basic framework of an imaging system to provide pressure measurements. Although any suitable optical or imaging modality can be used with the contemplated invention(s), optical coherence tomography (OCT) is described as an illustrative example of how the invention is compatible with an imaging system. As such, a general overview of OCT is provided below, followed by a description of the optical pressure sensor assemblies that can be used with OCT or other imaging systems. It is to be appreciated, that the OCT discussion is for illustration purposes and not limiting the invention to any specific imaging modality.

I. OCT System General Overview

OCT has been proposed as one technique that may be particularly helpful for imaging regions of tissue, including within a body lumen such as a blood vessel. At a basic level, OCT relies on the fact that light traveling from a source and scattering from more distant objects takes longer to travel back than light scattering from nearby objects. Due to the wave nature of light, very small timing differences caused by light signals traveling different distances on the micron scale can cause constructive or destructive interference with reference light signals. OCT systems measure the resulting interference to obtain an image of the target. A typical OCT system requires one or more interferometers to distinguish the signal from the applied light.

Figure 1:
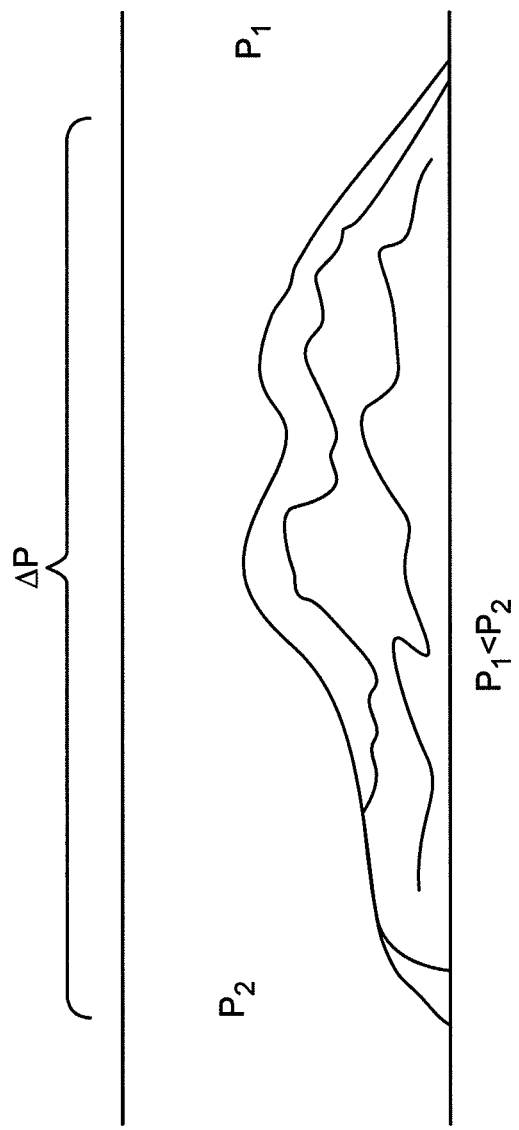
FIG. 1 illustrates a vessel lumen with a first and second pressure.
Figure 2:
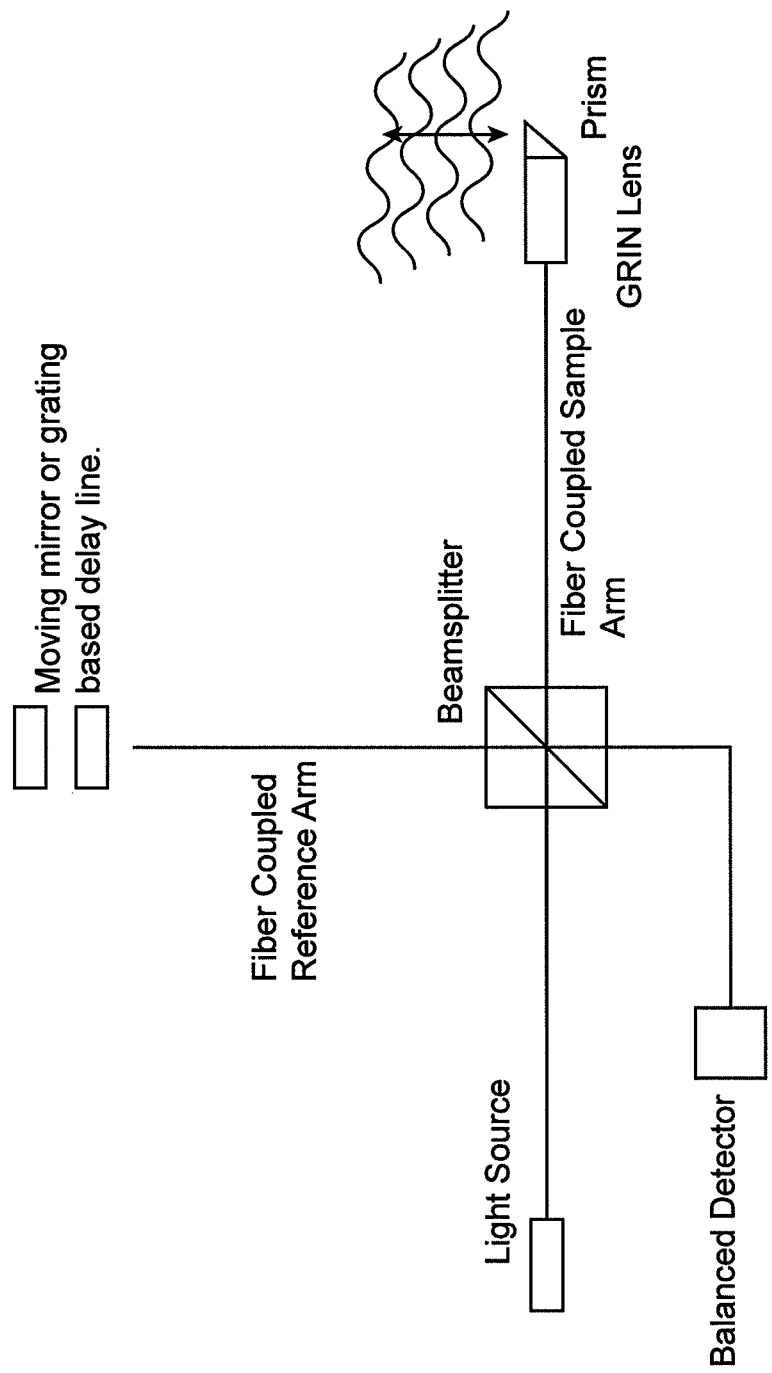
FIG. 2 is a schematic diagram of an interferometer.

Referring to FIG. 2, a general OCT device includes a target arm and a reference arm to generate a reference signal. In order to provide the interference reference signal, the OCT device will split an illuminating light signal from the source in two equal or unequal parts, send part of the illuminating light to the target of interest through one target optical "target arm" and send the other part of the illuminating light down a separate reference arm. Light from the separate reference arm reflects off of a mirror, and then returns and interferes with the scattered light that is returning from the target optical arm after bouncing off of the target. In a traditional OCT device, the reference arm length is engineered to be exactly the same length as the target arm so that the interference effect is maximized. The resulting interference between the two beams creates interference effects known as fringes that can be used to measure the relative reflectivity of various layers of the target. Using this information, an image of the object can be generated.

In addition, most known OCT systems, when applied to catheters, include a fiber that is rotated (often at high rates) within the catheter in order to scan around a lumen. During a medical procedure, such a cardiovascular catheter is typically removed from the factory sterile container. The proximal end of the catheter is connected to equipment needed to control the catheter (which in this case would also include the link to the OCT engine used to drive any OCT optical fiber in the catheter), and the distal tip is immediately inserted into the patient's body. The catheter is then discarded once the procedure is complete.

Figure 3:
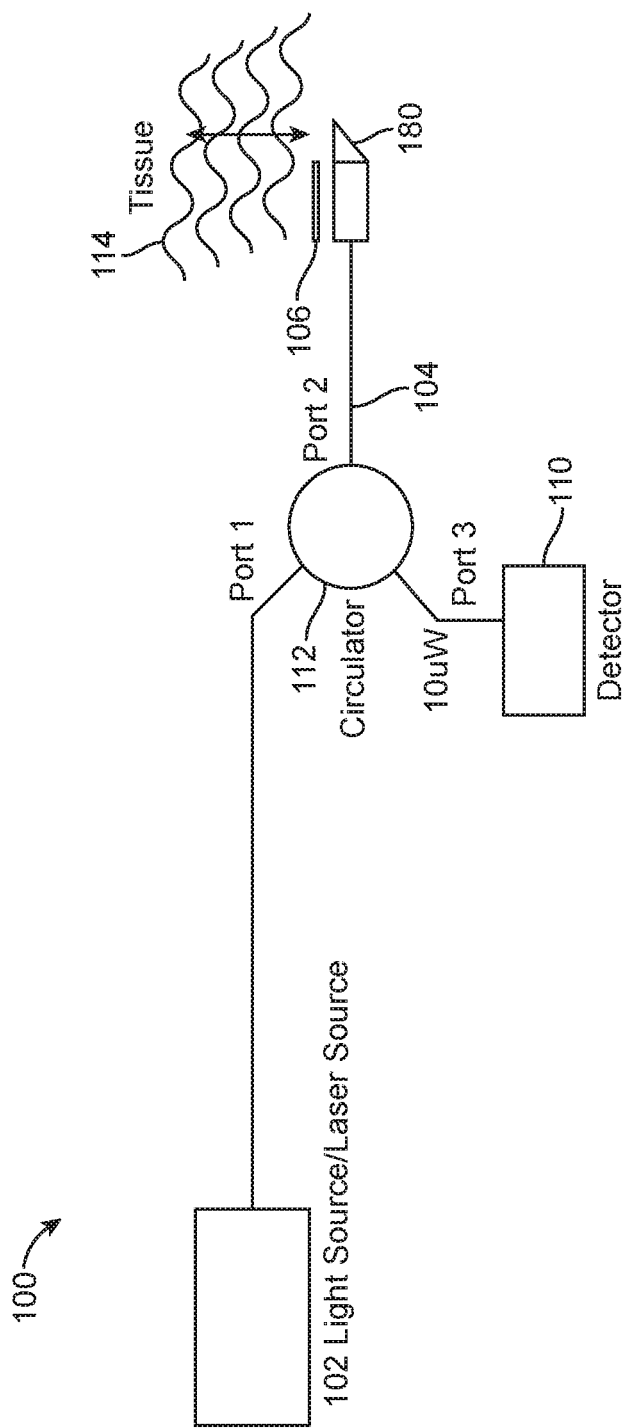
FIG. 3 is a schematic representation of an OCT catheter.

FIG. 3 provides a general illustration of a cardiovascular catheter that utilizes OCT for imaging. A common-path OCT system 100 includes a laser source 102, such as a swept frequency light source. An optical fiber 104 transfers optical radiation from the laser source 102 to the target 114. In some embodiments, the optical fiber 104 is a side-firing fiber that emits optical radiation from an angle relative to the longitudinal axis of the fiber 104. For example, the fiber 104 may transmit light at 90 degrees to the longitudinal axis. In other embodiments, the optical fiber may transmit in a straight path to a mirror 180 that reflects the transmitted light to the target 114. Some of the light beam that exits the optical fiber 104 will encounter the target 114 and be reflected or scattered by the target 114. Some of this reflected or scattered light will, in turn, reenter the tip of the optical fiber 104 and travel back down the fiber 104 in the opposite direction.

A Faraday isolation device 112, such as a Faraday Effect optical circulator, can be used to separate the paths of the outgoing light source signal and the target and reference signals returning from the distal end of the fiber. The reflected or scattered target light and the reflected reference light from the fiber can travel back to a detector 110 located at the proximal end of the optical fiber 104.

Because the reflected or scattered target light in the OCT system 100 travels a longer distance than the reflected reference light, the reflected or scattered target light can be displaced by frequency, phase and or time with respect to the reference beam. For example, if swept-source radiation is used, then the light from the target will be displaced in frequency. The difference in displacement in phase, time or frequency between the reflected or scattered target light and the reference light can be used to derive the path length difference between the end of the optical fiber tip and the light reflecting or light scattering region of the target. In the case of swept source OCT, the displacement is encoded as a beat frequency heterodyned on the carrier reference beam. Additionally, a computer or other processor may receive data corresponding to the reflected light in order to generate images of the target or to perform computations with the received data.

The laser source 102 can operate at a wavelength within the biological window where both hemoglobin and water do not strongly absorb the light, i.e. between 800 nm and 1.5 μm. For example, the laser source 102 can operate at a center wavelength of between about 1300 nm and 1400 nm, such as about 1310 nm to 1340 nm. In various embodiments, where the imaging modality is not OCT, the light source does not have to operate in a biological window, rather any wavelength of light can be used to provide light to the optical pressure assemblies described.

Additionally, the optical fiber 104 can be a single mode optical fiber for the ranges of wavelengths provided by the laser source 102. The optical fiber may have a cut-off less than 1260 nm and have single mode performance between 1270 and 1380 nm (and be manufactured compatible with SMF-28 standards).

II. Optical Pressure Sensor Assembly

As described above, one of the challenges for intravascular pressure measurement is the need for a pressure sensor that avoids the drawbacks of electrical interference such as drift, which affects the accuracy and reliability of electrical pressure sensors. To address this need, embodiments described provide for an optically-based pressure sensor that uses interferometry to determine intravascular pressure. In particular, the contemplated pressure sensor uses light reflected or scattered from an elastic membrane deflected by vessel pressure to determine blood pressure at target vessel locations. Because the mechanism is light-based, electrical disturbances like drift are avoided.

Generally, the pressure sensor assembly includes an elongate body such as an elongate housing or catheter. The elongate body is hollow or includes a lumen through which an optic fiber extends. The body includes an opening or hole, which is covered by an elastic membrane. The elastic membrane may only cover the hole or, alternatively, the elastic membrane may extend around the body to cover the hole as well as other portions of the body. The elastic membrane is adapted to move, deflect, or change shape in response to pressure exerted against the membrane.

In operation, positive intravascular fluid pressure pushes against a surface of the membrane exposed to the intravascular environment. The positive fluid pressure depresses or deflects the membrane toward an interior of the elongate body such as toward a central longitudinal axis of the body.

To provide optical pressure sensing, the optical fiber inside the body has a light emitting end aligned with the elastic membrane to allow the transmission of light from the fiber end to the elastic membrane. A light beam emitting from the fiber end will encounter the elastic membrane, which results in absorption, scattering, and reflection. Some of the reflected or scattered light will re-enter the light emitting end of the fiber to travel back down the fiber toward a proximal end of the fiber. The interaction of a reference light and the reflected/scattered light from the membrane is detected and used to determine the membrane deflection distance, which is used to compute the intravascular pressure exerted on the membrane.

Advantageously, the optical pressure sensors/assemblies can be used as standalone devices that are fed into a patient's vasculature to measure blood pressure at specific vessel locations. The pressure sensor assemblies may be used with an imaging system that provides a light source and electronics for detecting reflected/scattered light and computing pressure measurements.

Additionally, the described optical pressure sensor/assemblies are compatible for use with the existing architecture of intravascular devices (without or without imaging capability). In some embodiments, the pressure sensor assembly can be dimensioned to fit inside a lumen, such as a guidewire lumen, of an intravascular device. The pressure sensor assembly is advanced through the device lumen into a patient's vasculature. Once a pressure measuring end of the assembly is exposed in the vessel, pressure readings can be taken for that location. Where an intravascular device includes an optical interferometry system such as OCT, the pressure sensor assembly may use the existing light source and other components of the imaging system to measure and compute pressure. Alternatively, where the intravascular device is not equipped for imaging, the pressure sensor assembly may include an optical/imaging system for providing light, detecting reflected/scattered light, and computing intravascular pressure. In further embodiments, the optical pressure sensor assembly also functions as a guidewire.

In another variation, the pressure sensor assembly may be integrated into an intravascular device such that the device has built-in pressure measuring capabilities. For example, the pressure sensor assembly components can be integrated with an OCT imaging and occlusion-crossing catheter device, such as those described in U.S. patent application Ser. No. 13/433,049, titled "OCCLUSION-CROSSING DEVICES, IMAGING, AND ATHERECTOMY DEVICES," filed Mar. 28, 2012. The integrated device may include a catheter having a tip portion with an opening covered by an elastic membrane. An optical fiber resides within the body of the catheter with a light emitting end aligned with the opening and membrane. In one mode, the integrated device measures pressure while the device is rotationally fixed. In another mode, the integrated device generates OCT images by rotating the tip portion. In such cases, the optic fiber serves both as a pressure sensor and an OCT imaging sensor. Additionally, the integrated device may operate as part of an integrated system having components to control the integrated device, compute pressure, and generate OCT images.

Figure 4:
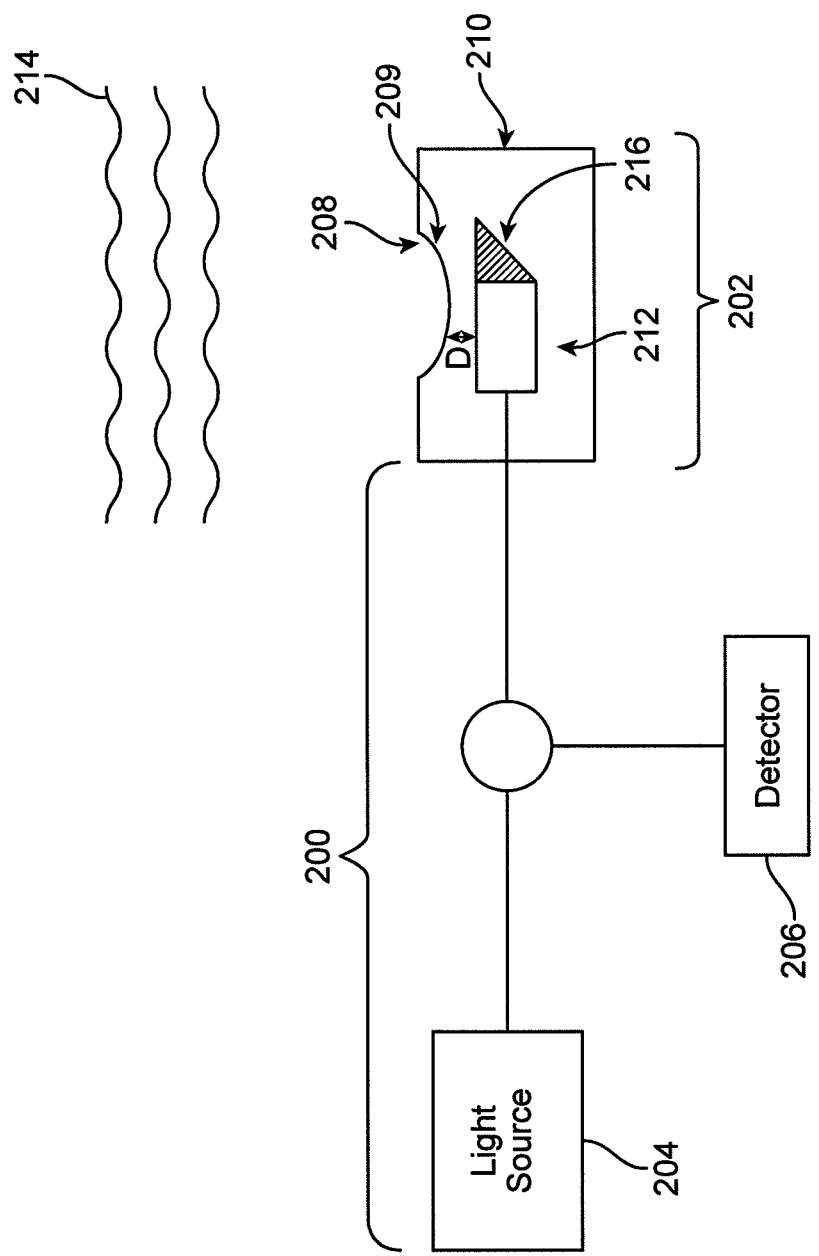
FIG. 4 schematically shows a general optical pressure sensor assembly.

Referring now to FIGS. 4-10, these illustrate schematically the general assembly components and methods by which the optical pressure sensor assembly measures intravascular pressure. FIG. 4 shows a general pressure sensor assembly 202 that is connected to an optical/imaging system 200. The imaging system 200 includes a light source 202 and a detector 206, and can be an OCT imaging system that is used to interchangeably generate images of the vascular lumen and measure intravascular pressure.

The pressure sensor assembly 202 includes an optical fiber 212 that is coupled to the imaging system 200. The optical fiber 212 is surrounded by a housing 210 that includes an opening 209 at a distal tip of the housing. The opening 209 is covered by an elastic membrane 208 that can deflect or move in response to pressure from the intravascular environment.

Any suitable membrane shape is acceptable provided that the membrane shape distorts to decrease the distance between the membrane and the fiber when the membrane experiences pressure. In some embodiments, the membrane is configured to adopt a concave shape or meniscus shape when pressure is exerted against a surface of the membrane, such as a top surface exposed to a surrounding intravascular environment. In a neutral non-deflected state, the membrane can have any shape including a relatively straight or slightly curved profile. In various embodiments, the membrane may be adapted to measure pressure between 40 mmHg to 250 mmHg or 60 mmHg to 200 mmHg.

As shown in FIG. 4, a distal end or light emitting end of the fiber 212 is aligned with the opening and membrane such that the fiber distal end is positioned near or below the membrane. Where a side-firing fiber is used, light emitted from the distal end of the fiber is directed toward the membrane and opening. In other variations, a mirror 216 is included in the distal tip to reflect light towards the elastic membrane 208. A mirror 216 may be used to redirect light from a front-firing fiber to the membrane 208.

In practice, the light source 204 provides optical radiation/light for transmission through the optical fiber 212. At the light emitting fiber end, some of the transmitted light will be reflected back from the distal tip or the circumference at the distal tip (in case of a side-firing fiber) of the fiber, hence forth referred as reference surface to create a first signal that serves as a reference signal for the pressure sensor assembly.

In some embodiments, the reference reflected light or reference signal is created by a common-path OCT system 100 shown in FIG. 3. The index of refraction of the interface medium 106 is different than the index of refraction of the distal edge of the optical fiber 104. Part of the light will exit the optical fiber 104 while part of the light will be reflected back from the distal end of the optical fiber 104, creating a reference reflection called a Fresnel reflection. In some cases, a GRIN fiber can be used to generate the Fresnel reflection.

In the common-path OCT system the optical fiber has a core providing a common path for optical radiation reflected from a reference interface and a target. The core has a first refractive index, $n_1$. The distal tip of the optical fiber is surrounded by interface medium such as an adhesive. The interface medium has a second refractive index $n_2$. Part of the light that exits from the distal tip of the fiber is reflected back due to Fresnel reflection. When the incident and thus the reflected light are perpendicular intensity of reflection can be given by the Fresnel equation shown below.

$$R = \left(\frac{n_1 - n_2}{n_1 + n_2}\right)^2$$

For common path OCT the first refractive index and the second refractive index are mismatched such that the reference reflection lies between −28 dB and −38 dB. This ensures optimal operation of the receiving electronics of the common path OCT system are described in U.S. patent application Ser. No. 12/790,703, filed May 28, 2010 and titled "OPTICAL COHERENCE TOMOGRAPHY FOR BIOLOGICAL IMAGING", Publication No. US-2010-0305452-A1.

Some examples of the adhesive used as an interface medium are Masterbond EP42HT-2, EpoTek OG127-4 or OG116, produced by Epoxy Technology, Billerica Mass. and UV curable photonics adhesive OP-4-20658, produced by Dymax corporation, Torrington Conn.

In addition to the reflected reference light described above, some of the light exiting the fiber 212 encounters a surface or region of the elastic membrane 208. Some of this light will be reflected or scattered by the elastic membrane and re-enter the fiber 212, traveling down the fiber 212 in the opposite direction to generate a second signal, wherein the second signal represents light reflected/scattered by the membrane.

As shown in FIG. 4, the elastic membrane is separated from the optic fiber by a variable distance D. Unlike the reference reflected light, light reflected or scattered from the membrane must cross distance D (i.e. light pathway length) between the fiber and the membrane. This results in differences in the wave properties between the first reference signal and the second signal generated from the membrane. For example, the first and second signals may differ in phase, time, and/or frequency.

In general, the housing may be sealed so that the pressure inside the housing is known and/or constant. The tip of the fiber optic from which light is emitted and received may be fixed within the housing, for example, to a wall of the housing that is opposite to the membrane-covered opening. In some variations the housing is sealed completely, with a known pressure, which may allow a pressure measurement relative to the known pressure. In some variations the interior of the housing is open to atmosphere pressure at the proximal end of the elongate device (e.g., near the light source), providing pressure relative to external pressure.

Figure 5:
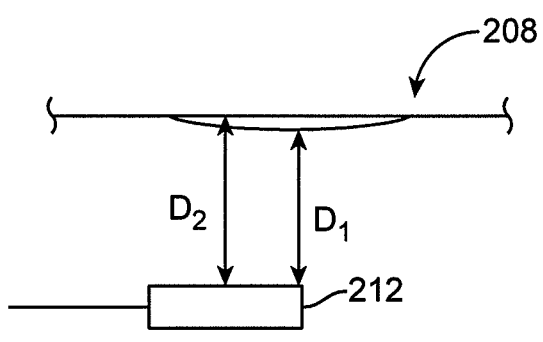
FIG. 5 illustrates the deflectable membrane and an optical fiber in an optical pressure sensor assembly.
Figure 6:
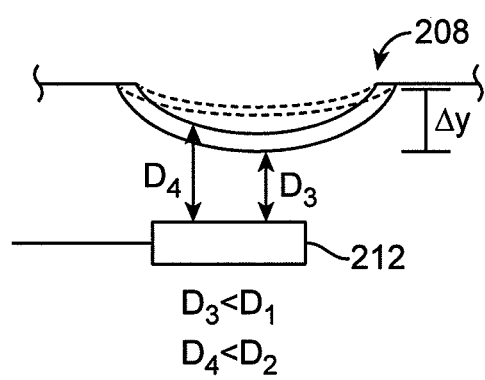
FIG. 6 shows the optical pressure sensor assembly of FIG. 5 with a deflected membrane.

Moreover, an interference signal is generated from the interaction of the first and second signals. As described, the first reference signal is generated at the distal end of the fiber. This is also where the second signal from the membrane re-enters the fiber. When the two signals meet, an interference signal is generated. The resulting interference signal from the reference reflection and the back-scattered light from elastic membrane is displaced in phase, time or frequency which can be measured to find precise distance D between the end of the optical fiber tip, which is stationary with respect to the housing, and the deflected membrane. Referring to FIGS. 5-6, the distances between the elastic membrane 208 and the fiber 212 are shown for a neutral state elastic membrane (FIG. 5) and a deflected elastic membrane (FIG. 6). Although FIG. 5 shows the membrane deflected, in some variations the membrane may be non-deflected (e.g., smooth across the opening into the housing) or may bulge outward (e.g., housing pressure greater than external pressure). In FIG. 5, the distances D1 and D2 indicate the neutral or non-deflected pathway lengths between the optical fiber 212 and the elastic membrane 208. D1 and D2 are shown measured at different points (laterally) along the surface of the membrane; in practice D1 and D2 may be measured from the same portion of membrane. The elastic membrane 208 has two surfaces from which light can scatter or reflect. D1 is the distance between reference surface on the fiber and 212 the bottom surface of the membrane 208. D2 is the distance between the reference surface on the fiber 212 and the top surface of the membrane 208. Although shown as having D1 and D2 from two surfaces, the pressure sensor assembly may only utilize the distance value for one of the surfaces as the thickness between the surfaces may stay relatively constant. The non-deflected state in FIG. 5 may serve as an initial reference configuration to which deflected orientations are compared.

FIG. 6 shows an example of a deflected membrane 208. In the deflected orientation, the elastic membrane 208 has a distance D3 and D4 between the reference surface on the fiber and the bottom and top surfaces respectively. As shown, D3 is less than D1 and D4 is less than D2. This change in distance is notated generally as $\Delta y$. Accordingly, $\Delta y$ indicates the amount of deflection or membrane deflection distance experienced by the elastic membrane 208. In some embodiments, the deflection amount $\Delta y$ is proportional to the force exerted on the membrane to deflect the membrane. Where force is intravascular pressure, the membrane deflection distance can be used to calculate the pressure at the specific vessel location. For example, the pressure sensor assembly 202 can be calibrated such that the pressure per deflection distance relationship is known and can be used to compute pressure once $\Delta y$ is determined by the imaging system 200. In some variations, the intravascular pressure is correlated to the difference between a first and second fiber-membrane distance, $\Delta y$. In other embodiments, a single distance between the fiber and the membrane is sufficient to determine pressure (e.g. D3 or D4 alone).

In some embodiments, one method for determining the distance D between the membrane and the light-emitting end of the optic fiber includes generating an interference signal as described above. As discussed, light is transmitted from the distal end of the fiber. Some of this light encounters an interface medium to generate a Fresnel reference reflection that provides a first reference signal. Additionally, some of the transmitted light passes through the interface medium and encounters the deflected surface of the membrane to reflect or scatter off regions of the deflected surface. Some of the scattered/reflected light will re-enter the optic fiber to form a second signal.

Because the reflected or scattered light (second signal) from the membrane travels a longer distance than the reflected reference light, the reflected or scattered target light can be displaced by frequency, phase and or time with respect to the reference beam. For example, if swept-source radiation is used, then the light from the membrane will be displaced in frequency. The difference in displacement in phase, time or frequency between the reflected or scattered target light and the reference light can be used to derive the path length difference D between the end of the optical fiber tip and the light reflecting or light scattering region of the membrane. In the case of swept source OCT, the displacement is encoded as a beat frequency heterodyned on the carrier reference beam, this creates the interference signal.

A detector, processor, controller, or other suitable electronic receives the interference signal and calculates the distance D based on the signal properties. For example, the greater the distance, the higher the beat frequency.

Continuing with the above example, once the distance D is known, this can compared with a non-deflected distance $D_0$ for the membrane. A deflection distance $\Delta y$ can be calculated from the deflected light path length D and non-deflected light path length.

Finally, pressure exerted to deflect the membrane can be computed by comparing the deflection distance $\Delta y$ to a predetermined deflection-to-pressure relationship or rate for the membrane. For example, where the $\Delta y$ is 60 microns and the deflection-pressure rate is 10 microns per 20 mmHg of pressure, the pressure is 120 mmHg. In some embodiments, the pressure sensor assembly includes a storage device storing the deflection-to-pressure rate for the assembly. The storage device may be on the assembly, such as on the housing, and is accessible by a processor, controller, or other electronics performing the pressure calculation.

As described in greater detail below, any appropriate membrane material, including materials having different deflection-to-pressure rates may be used. Different thicknesses of materials may also be used. In some variations, the housing may include multiple windows having multiple deflection-to-pressure rates and therefore different sensitivities or pressure ranges (which may overlap); each of these may be monitored or polled by the same or different optical fibers. Thus, multiple optical fibers may be used, or a single optical fiber that can be directed to different membrane-covered windows (e.g. by sliding axially within the housing, by rotating with the housing, etc.).

Figure 7:
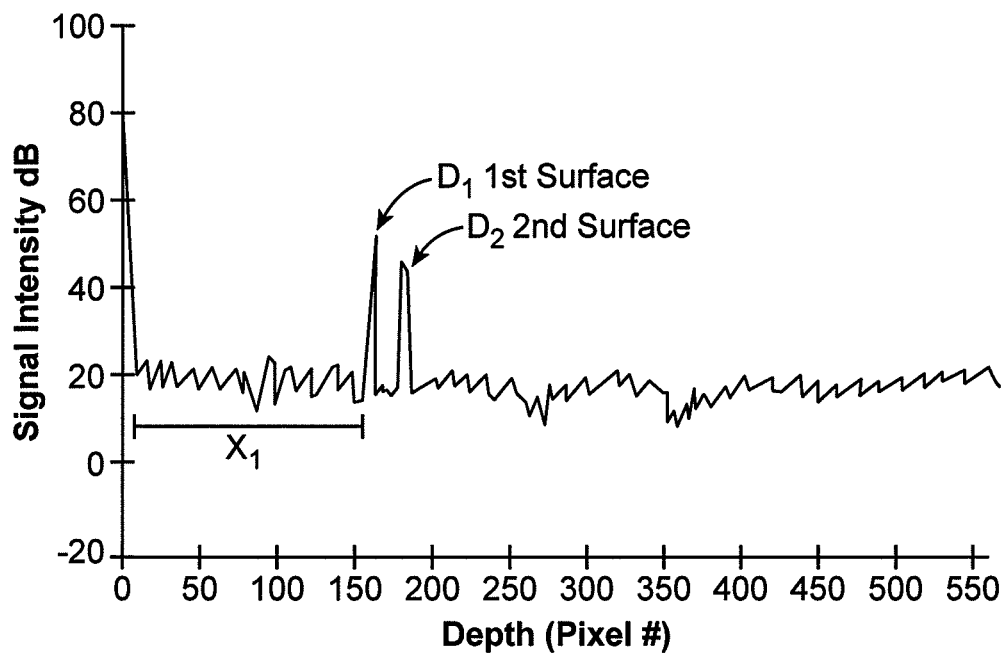
FIG. 7 is a schematic representation of signal intensity and depth values for the assembly in FIG. 5.
Figure 8:
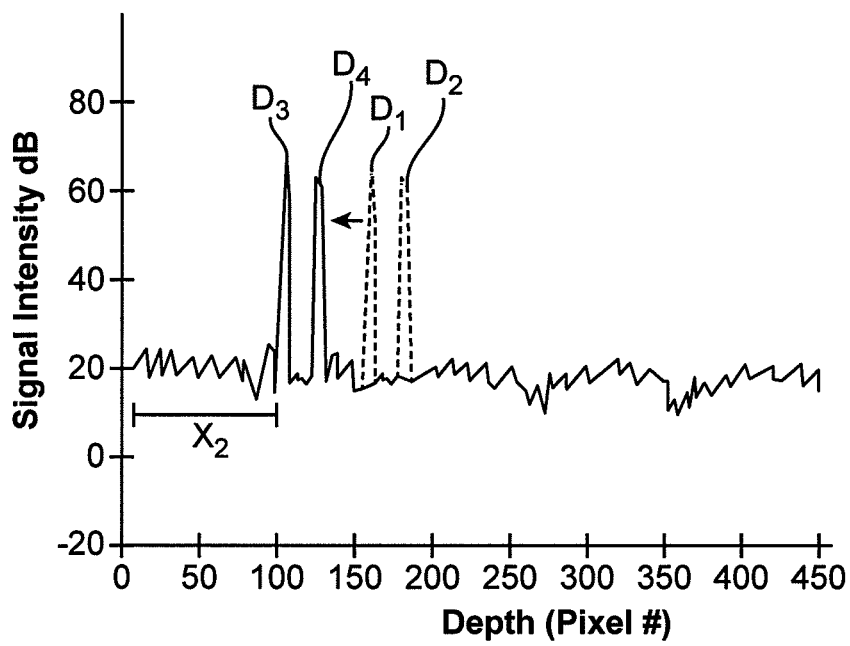
FIG. 8 is a schematic representation of signal intensity and depth values for the assembly in FIG. 6.
Figure 9:
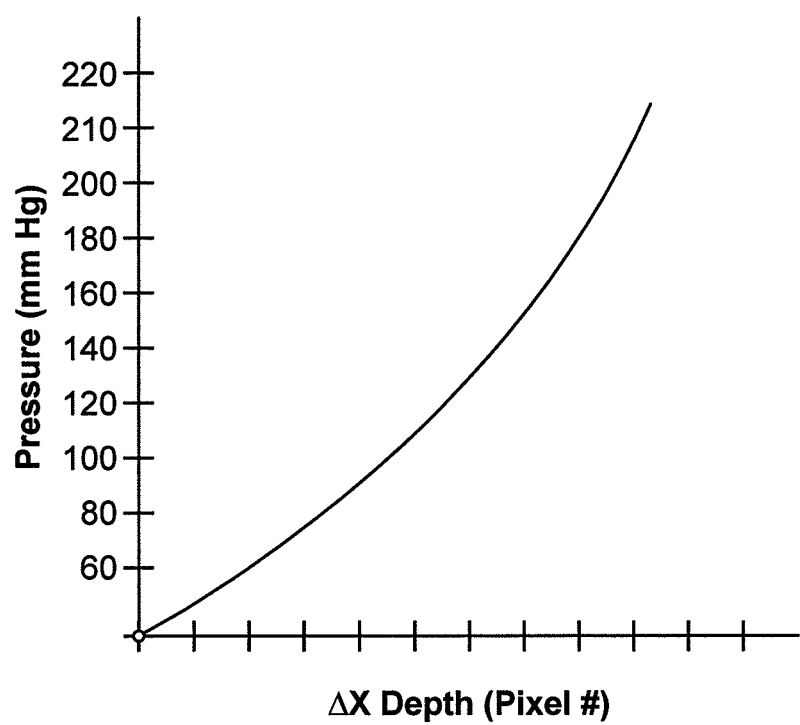
FIG. 9 is a schematic representation of pressure to depth values for a calibrated optical pressure sensor assembly.

Another related method for computing pressure is schematically shown in FIGS. 7-9. FIGS. 7-8 show the relationship between signal intensity in dB vs. pixel number depth. At the non-deflected position or a first position in the vessel, the two peaks indicate the reflected/scattered light received by the fiber 212 in FIG. 4. The first peak at about a depth of 150 indicates the first distance D1 (bottom surface) which is at a closer in depth than D2 (top surface) to the fiber 212. FIG. 8 shows the first and second peaks translated toward the y-axis for the deflected membrane. This is expected as the depth for the deflected membrane should be less than that of the non-deflected membrane as the deflected membrane is closer to the fiber and the light pathway lengths between the membrane and the fiber are shorter. The difference Δx between the peaks (X1-X2) is proportional to the pressure applied to deflect the membrane. As such the difference in D1 and D3 depth for the first peak can be used to compute the pressure exerted on the membrane. This may be achieved by comparing the Δx value to a pressure-deflection curve or relationship.

This pressure-deflection relationship can be predetermined for a pressure sensor assembly. This relationship may be stored as calibration information for the assembly. The calibration information and relationship may be stored on the assembly by way of a storage device such as Electrically Erasable Programmable Read-Only Memory (EEPROM) whereby a processor can access calibration information to determine measured pressure. FIG. 9 shows a graphical representation correlating blood pressure with the deflection of the membrane 208.

As can be appreciated, the optical pressure sensor assembly may communicate with a controller, processor, detector, or any other electronics. These electronics may receive data or signals regarding the light received in the optic fiber. These electronics may also be configured to carry out any of the calculations and computations described. Additionally, these electronics may also generate images such as OCT images.

Figure 11:
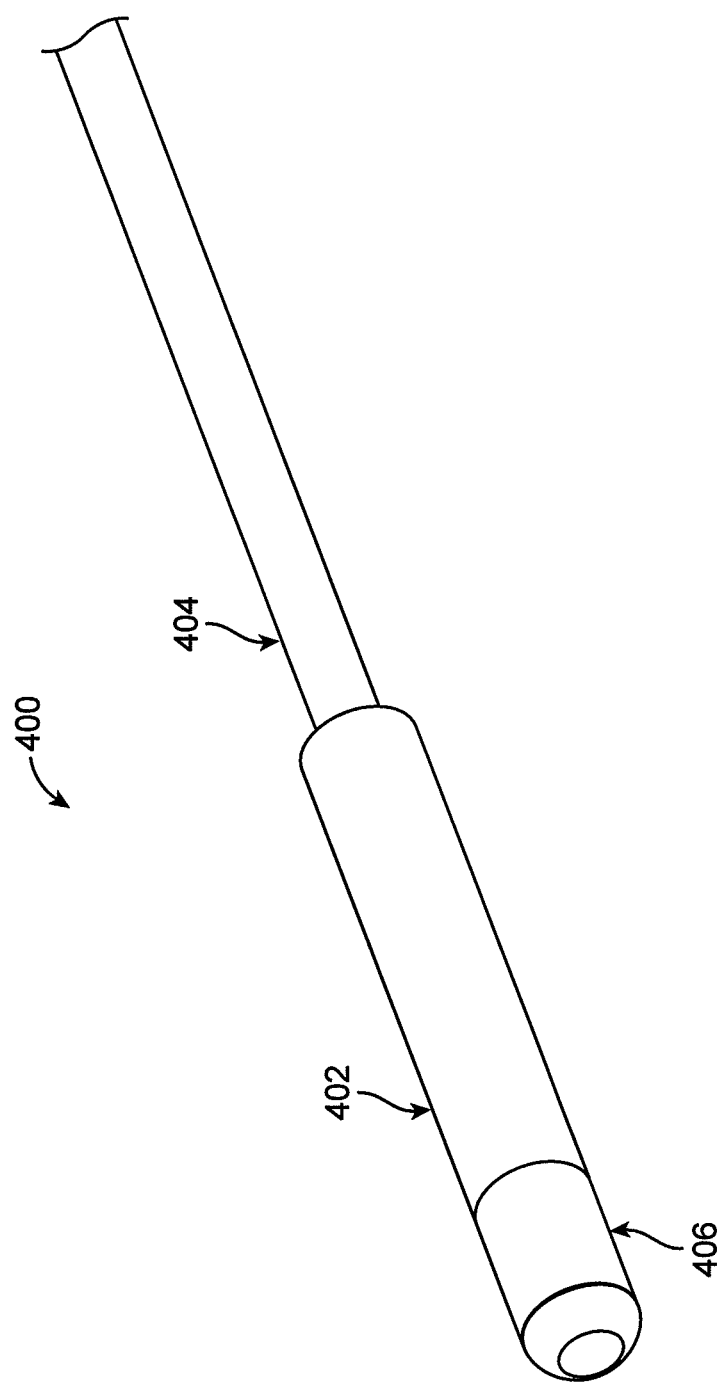
FIG. 11 is a perspective view of an optical pressure sensor assembly.
Figure 12:
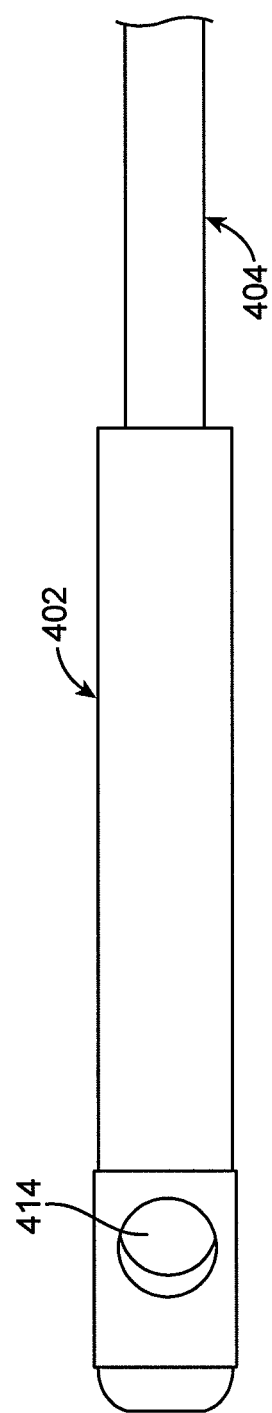
FIG. 12 is a top view of the assembly of FIG. 11 showing the opening in the housing.
Figure 13:
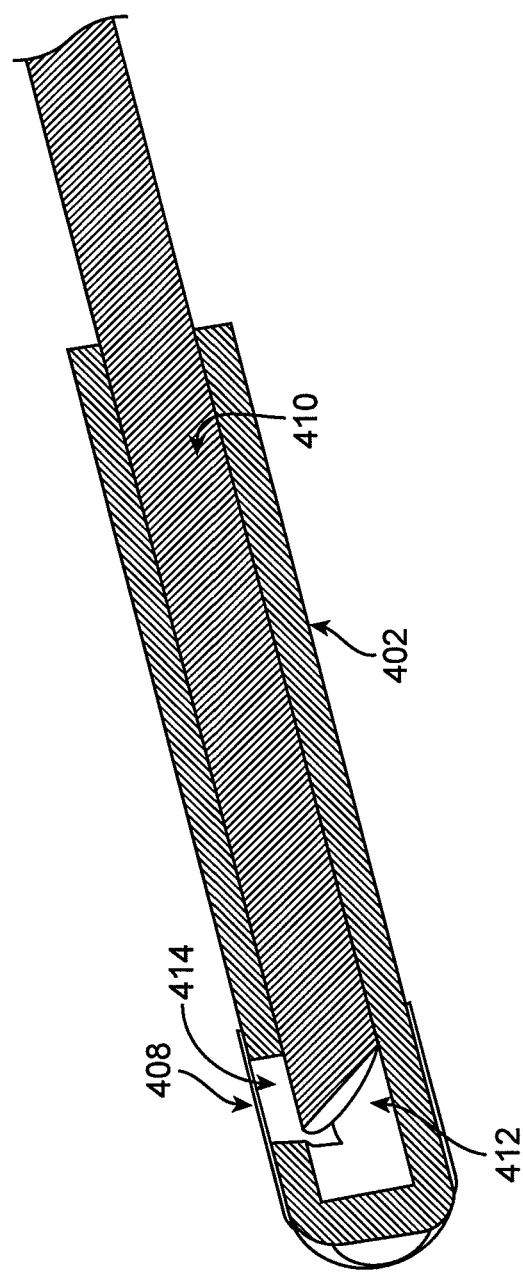
FIG. 13 is a cross-section view of the assembly of FIG. 11.
Figure 14:
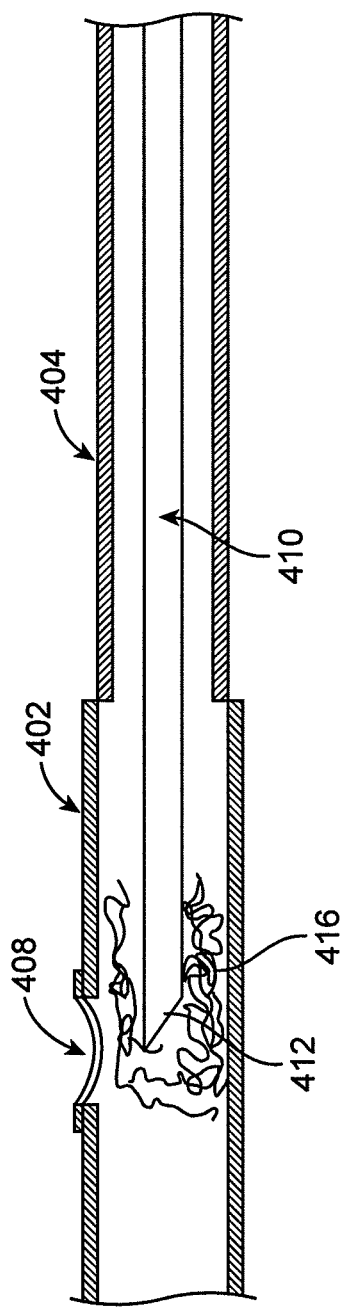
FIG. 14 is a cross-section view of an optical pressure sensor assembly according to some embodiments.

Referring to FIGS. 11-14, additional details regarding the components of the pressure sensing assembly are described. FIG. 11 shows an optical pressure sensor assembly for use with an optical imaging system. The optical pressure sensor assembly 400 includes an elongate body having a housing 402 and a covering 404 such as a hypotube. A distal tip of the housing 402 includes an opening 414 and an elastic membrane 408 positioned at the opening. An optical fiber resides within a lumen of the elongate body with a distal end 412 of the fiber 410 positioned near the opening 414 and elastic membrane 408. The distal tip of the fiber is completely encapsulated within an epoxy to generate the reference reflection (FIG. 14).

As shown, the elastic membrane 408 covers the opening 414. The material 406 for the elastic membrane 408 surrounds and encircles a circumferential portion of the housing 402. In other variations, the elastic membrane covers only the opening 414 without substantially extending around the housing. In additional embodiments, the elastic membrane is formed by inserting the housing 402 through heat shrink tubing and shrinking the tubing to cover the opening 414 and an outer surface of the housing. The heat shrink tubing may also be applied to cover the covering 404.

Any suitable material may be used for the elastic membrane 408 including biocompatible polymers such as FEP (fluorinated ethylene propylene), Tecothane®, and PET. In general, the membrane can be made from an elastic or resilient material (e.g. cross-linked polymer) that can recover from deflection induced by intravascular pressures. In some embodiments, the membrane recover from deflection by intravascular pressures between about 40 mmHg to about 250 mmHg. Additionally, any material that exhibits measurable deflection when pressure or force is exerted against the membrane can be used for the membrane. Because the pressure force will be in a range associated with blood pressure, the membrane may demonstrate a spring force or resilience that is suitable for measuring pressures between about 40 to about 250 mmHg. Additionally, the elastic membrane may have a thickness between about 10 microns to about 50 microns. Although described as an elastic membrane, the membrane may also be any suitable movable element such as a flexible or compliant diaphragm, sheath, meniscus, spring or other component that moves in response to blood pressure.

In some embodiments, the elastic membrane 408 forms a crescent-shape or meniscus shape across the opening 414 when deflected. The deflected elastic membrane 408 may dip or curve slightly to form a concave top surface and a convex bottom surface across the opening 414. Any suitable membrane shape is acceptable provided that the membrane shape distorts to decrease the distance between the membrane and the fiber when the membrane experiences pressure. In some embodiments, the membrane is configured to adopt a concave shape or meniscus shape when pressure is exerted against a surface of the membrane, such as a top surface exposed to a surrounding intravascular environment. In a neutral non-deflected state, membrane can have any shape including a relatively straight or slightly curved profile.

The opening 414 is generally sized to permit an elastic membrane to sit over the opening while supported by the housing 402 structure. The opening 414 may be any suitable size for achieving this purpose including between about 100-500 microns, 200-400 microns, or 100-200 microns. Generally, the opening is sized to allow a light beam to exit the opening. As shown, the opening is formed on the housing 402 through the side wall of the housing 402. Additionally, the opening can have a circular, oval, and/or elliptical shape. However, the opening is not limited to these shapes.

As shown in FIG. 13, the opening 414 is positioned at about 90 degrees relative to a central longitudinal axis through the housing 402. This is particularly useful where OCT images can be generated by the pressure sensor assembly when the housing 402 is rotated within a vessel lumen. However, the opening is not limited to a side position. The opening can be placed at the end of the distal tip on the central longitudinal axis of the housing. In such cases, the fiber may transmit and receive light through a distal end of the fiber facing the opening. Such variations can be used with non-OCT imaging systems that employ interferometry.

FIG. 13 shows the optical fiber 410 with distal end cleaved at an angle such as 45 degrees and the end surface is polished and coated with reflective material such as Gold. The angle polish/cleave with gold coating allows the light to be reflected at an angle such as 90 degrees to the longitudinal axis of the fiber. The distal end of the fiber 412 is placed near the opening 414. The optical fiber may reside in a central or off-axis lumen through the housing. The fiber may be adhered or otherwise mechanically secured to the assembly. In some embodiments, an interface medium such as an adhesive 416 is placed at the firing end of the fiber to create a Fresnel reference reflection as described in detail above.

Additionally, the optical fiber 410 can be a single mode optical fiber for the ranges of wavelengths provided by the light source. The optical fiber may have a cut-off less than 1260 nm and have single mode performance between 1270 and 1380 nm (and be manufactured compatible with SMF-28 standards).

In yet another embodiment, a front-firing fiber, such as optical fiber cleaved between 0 and 2 degrees may be used in conjunction with a mirror for reflecting light through from the opening on the side of the housing. FIGS. 22A-D show an exemplary optical pressure sensor assembly 2500 having a hollow elongate body 2502 with a distal tip 2504. The distal tip 2504 including an opening 2508 covered by a resilient sheath 2510. The resilient sheath is adapted to distort or deflect when intravascular pressure is exerted against the sheath.

Figure 22A:
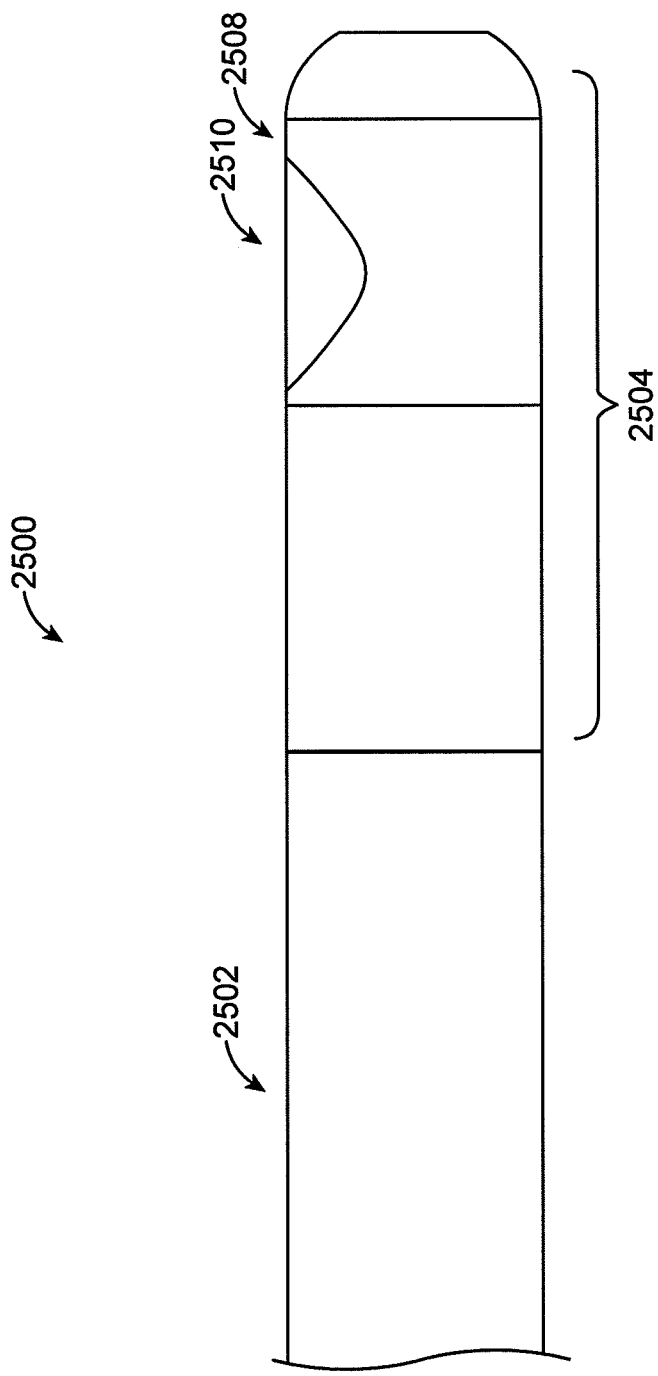
FIGS. 22A-D show a pressure sensor assembly with a front-firing optical fiber.
Figure 22B:
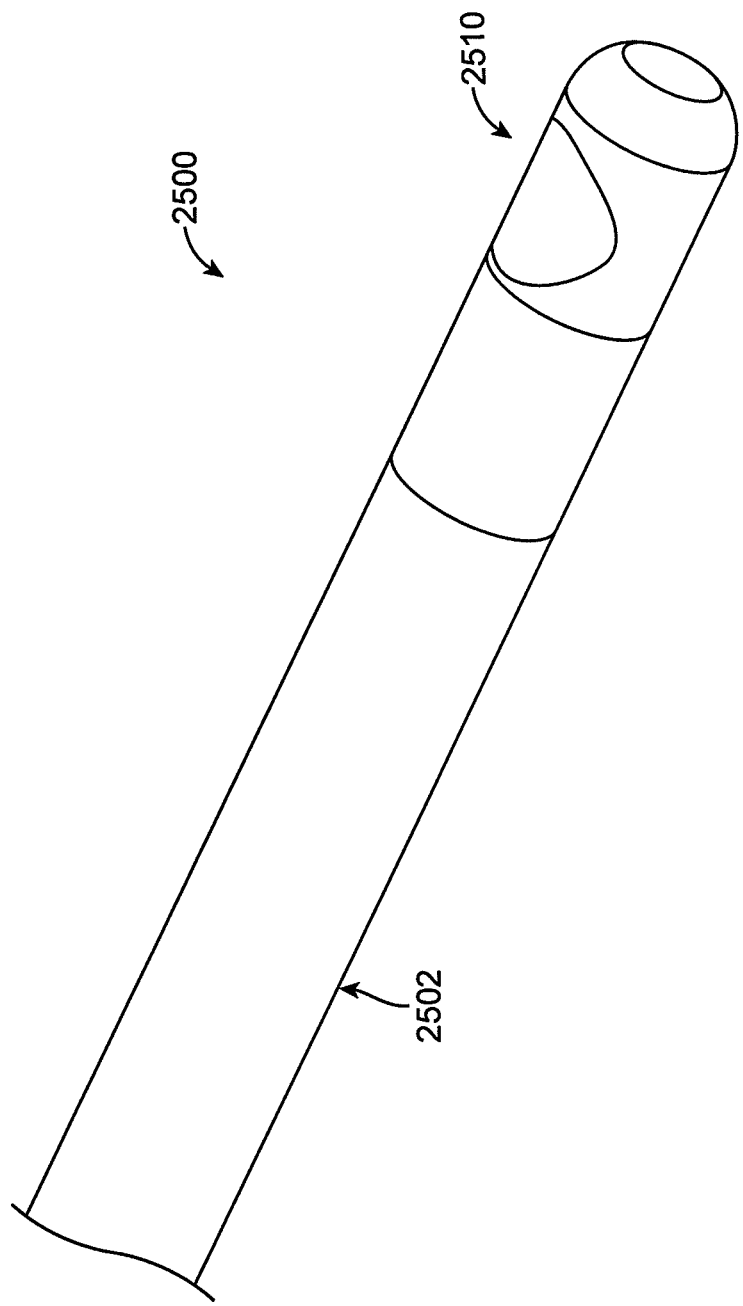
Figure 22C:
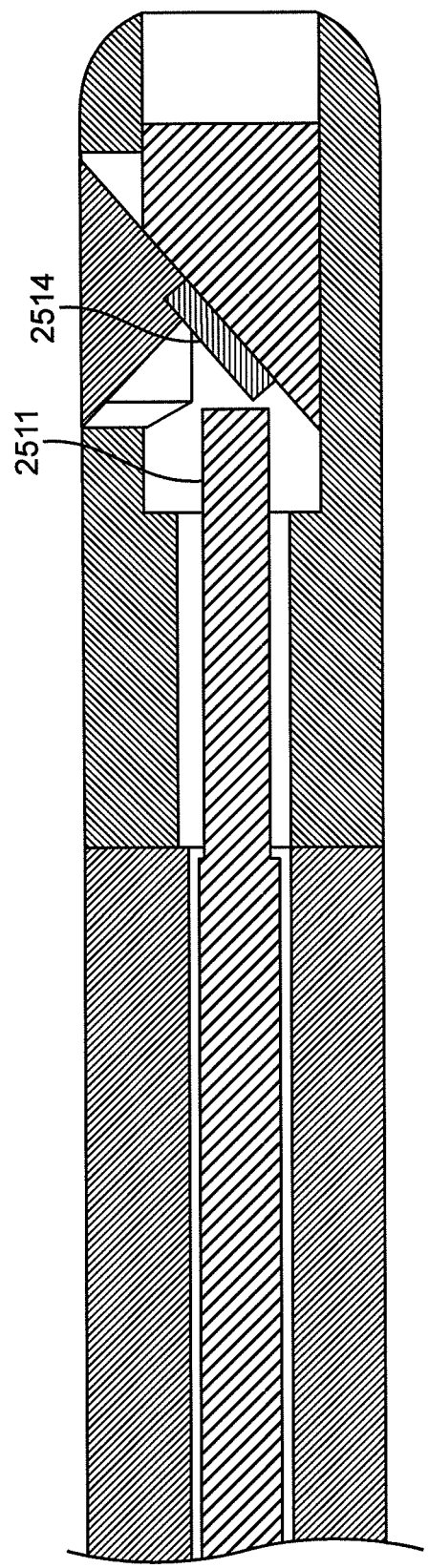
Figure 22D:
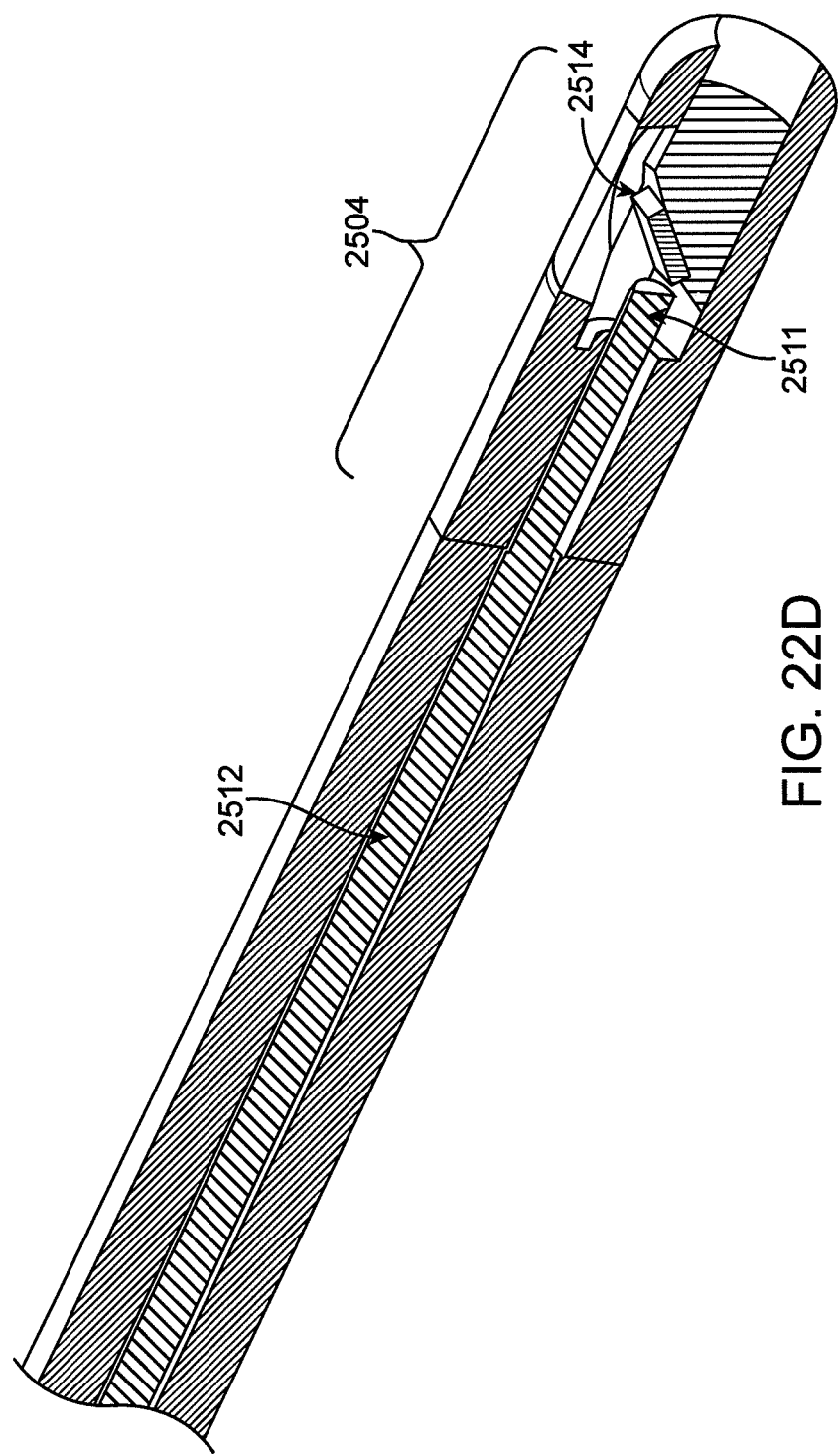

Referring to the cross-sectional views in FIGS. 22C-D, an optical fiber 2512 resides within a lumen inside the elongate body. The optical fiber has a front-firing distal end 2511 that emits light to a mirror 2514. The mirror 2514 is positioned to reflect light at an angle towards the membrane. Additionally, the mirror 2514 directs light that is reflected/scattered back from the membrane into the distal end 2511 of the optic fiber 2511.

Furthermore, to use the pressure sensor assembly with an optical/imaging system, the assembly may include optical and electrical connectors to transfer light and power from the imaging system to the assembly.

Figure 15:
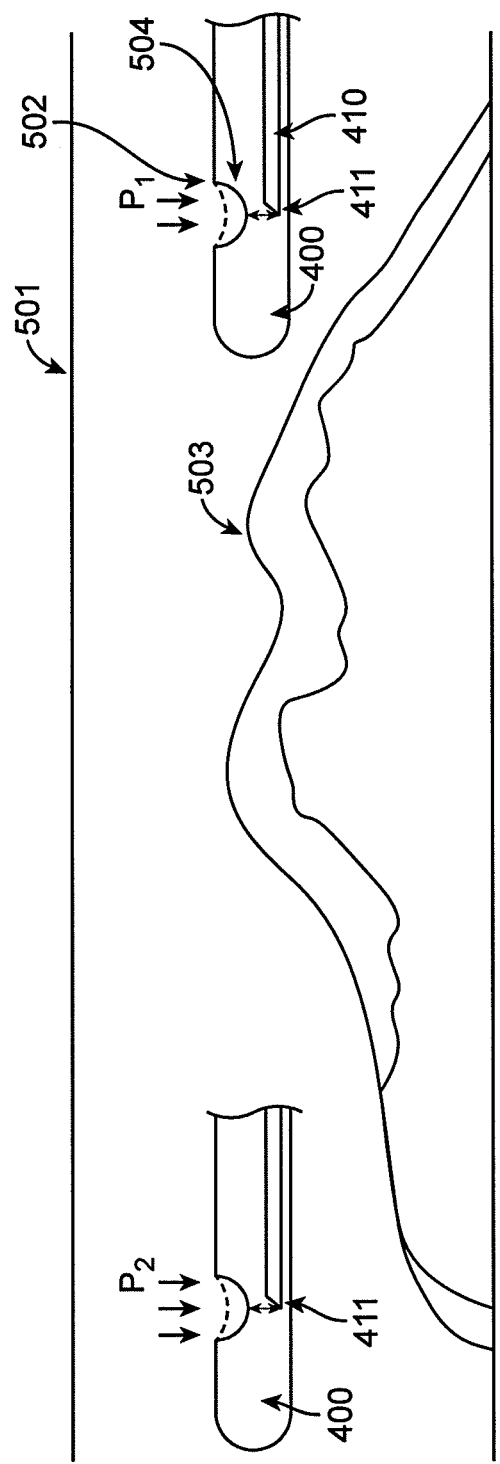
FIG. 15 shows a vessel with an optical pressure sensor assembly measuring pressure at two locations.

In operation, the optical pressure sensor assembly 400 measures blood pressure by detecting reflected/scattered light from the elastic membrane and computing the distance between the deflected elastic membrane and the distal tip of the optical fiber. Referring to FIG. 15, in the un-deflected or neutral state, the elastic membrane provides a reference distance 502 between the membrane and the firing end 411 of the optical fiber 410. Increased pressure P1 exerted against the outside surface of the elastic membrane, which is in direct contact with blood, pushes down against the elastic membrane to deflect and distort the membrane towards the reference surface on the optical fiber 410. The changed distance between the elastic membrane and the reference surface is proportional to blood pressure.

In practice, pressure measurements at two locations are taken for comparison to determine the pressure ratio or gradient caused by an occlusion. In some cases, a measurement is taken on either side of an occlusion. FIG. 15 shows a first pressure P1 taken at a first location and a second pressure P2 taken at a second location on the other side of the occlusion. Alternatively, the first and second measurements may be taken on the same side of the occlusion. The first measurement may be taken to determine a baseline pressure for the patient and the second measurement is taken near or at the occlusion to determine the increased pressure caused by the blockage. The baseline pressure is compared to the second measurement to compute a ratio or gradient.

As discussed, a processor, computer, or other electronic component may be used to calculate pressure. The processor may compute the measured deflection with reference or calibration data for the pressure sensor assembly. Reference or calibration data for the assembly can include the pressure-membrane deflection relationship for the specific assembly. This data can be provided in a memory storage device such as EEPROM that is accessible by a processor or computer configured for computing the measured pressure(s). The memory storage device may be included in the body of the assembly, e.g. on the housing, for easy access by a processor.

Because the optical pressure sensor assembly is designed to be introduced into and advanced through a patient's vasculature, the assembly may employ a catheter as the main body for containing the described components. The catheter can be dimensioned to fit within vessels of the body, such as blood vessels. For example, the catheters can be configured to be placed within the peripheral blood vessels. Thus, the catheters can have an outer diameter of less than 0.1 inch, such as less than 0.09 inches, such as less than or equal to 0.08 inches.

Figure 10:
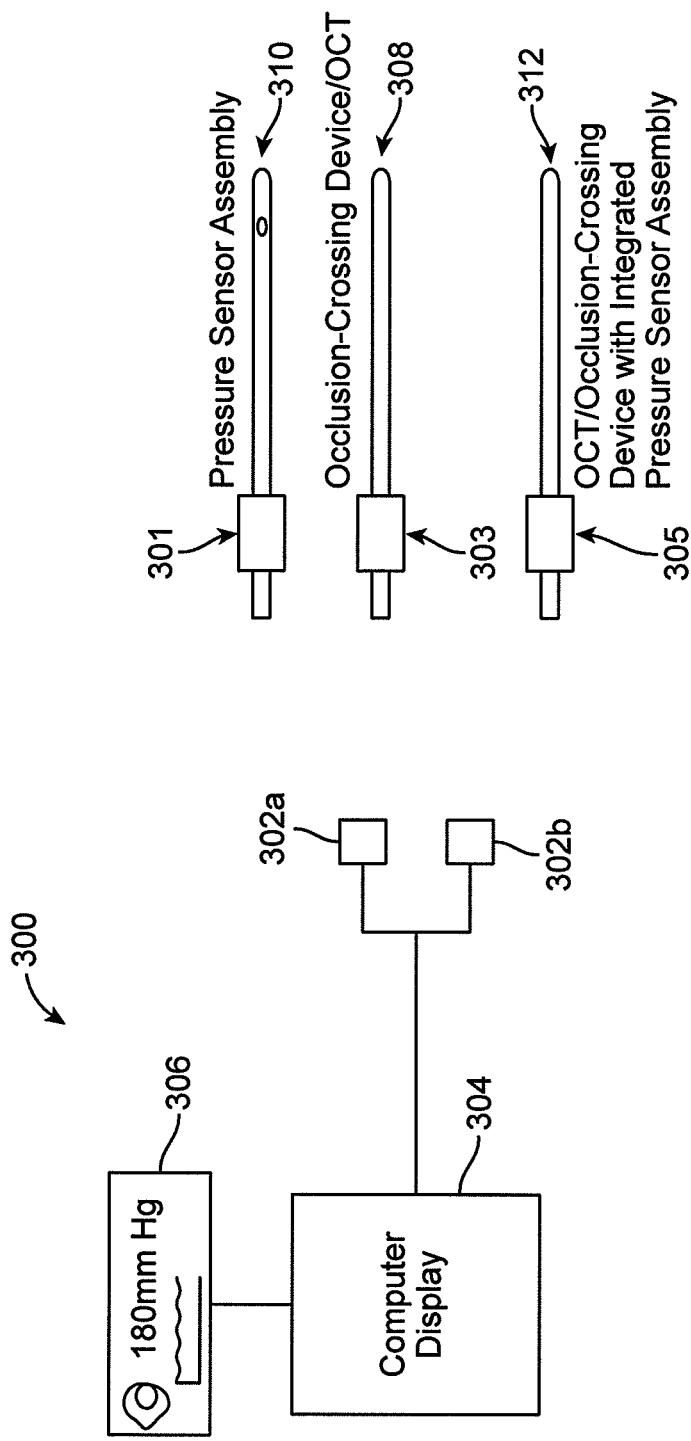
FIG. 10 shows an imaging system that can be interchangeably coupled to an optical pressure sensor assembly and other catheter devices.

Advantageously, as mentioned, the pressure sensor assemblies described can be used as a standalone device, as a complementary device for an existing intravascular device (e.g. occlusion-crossing or atherectomy catheters), or as part of an integrated intravascular device with pressure sensing capabilities. For example, FIG. 10 provides an example of a general OCT system 300 that can be used with these various embodiments. The OCT system 300 includes a console 304 that may include a computer or processor, light source, and display 306. The display may display OCT images or pressure values. The console 304 is in optical and/or electrical communication with a connector 302. In some cases, the console is in communication with a series of connectors 302a-b. The connectors 302a-b are adapted to couple to a corresponding or complementary connector on a pressure sensor assembly or intravascular device.

As shown, the OCT system can be used with the standalone optical pressure sensor assembly 310. The optical pressure sensor assembly may be any of the embodiments described; however, in FIG. 10, the pressure sensor assembly is configured for use with the OCT system. The optical pressure sensor assembly 310 can be coupled to one of the connectors 302a-b to receive power or light. Once connected to the light source, the optical pressure sensor assembly 310 can be used to measure intravascular pressure. This can be achieved by exposing a sensing portion of the assembly (e.g. distal tip having a deflectable membrane and optic fiber) to fluid pressure in a patient's vasculature and calculating the pressure based on optical properties of light scattered or reflected in the sensing portion. The OCT console (or separate controller) can be used to compute the intravascular pressure.

Alternatively, the optical pressure sensor assembly 310 may be used with the occlusion-crossing and OCT imaging catheter device 308. The OCT device 308 includes connectors 303 for optically and electrically coupling the device 304 to the controller 304. Although having occlusion-crossing or OCT capabilities, the catheter 308 is not equipped for pressure sensing. Because the OCT system has a light source, detector, applicable electronics, processors, etc., the imaging components of the OCT system can be used with the pressure sensor assembly 310 described to generate pressure measurements once the catheter 310 is advanced into the patient's vessel.

Figure 16:
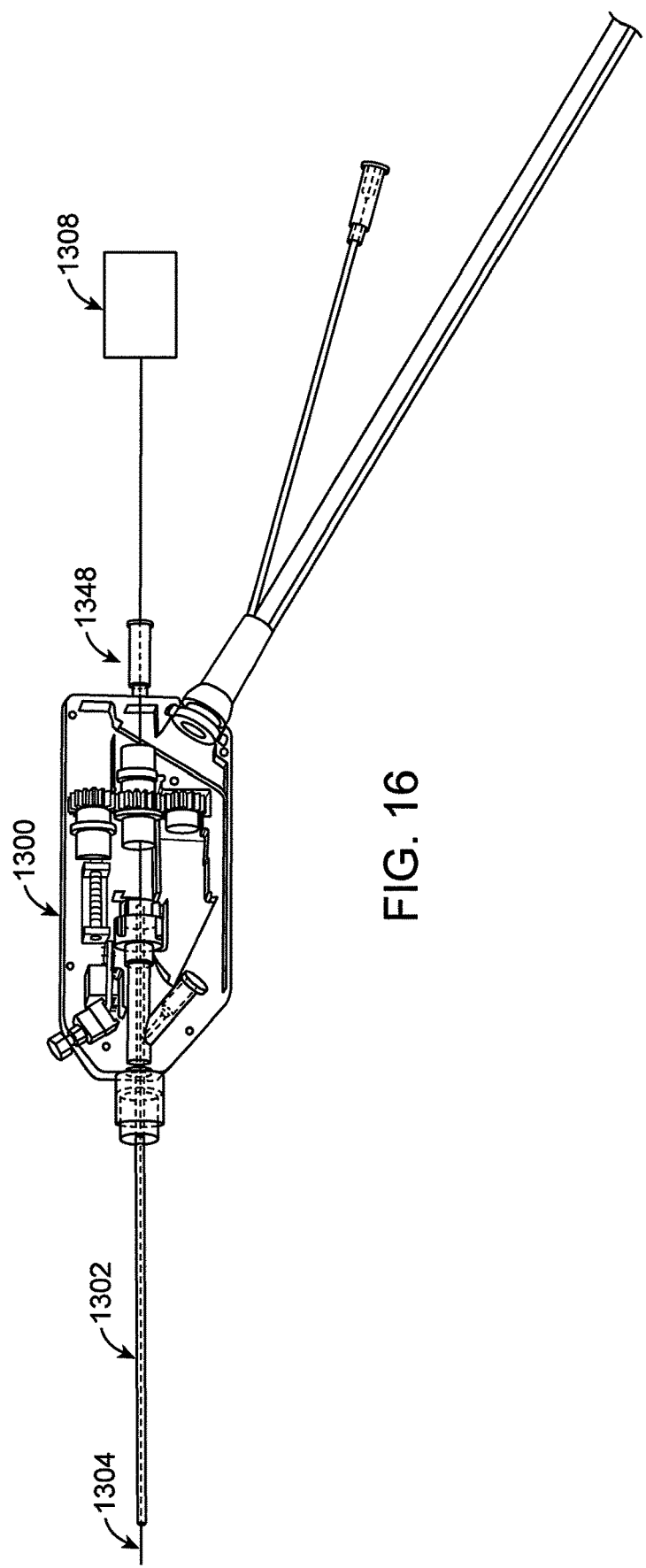
FIG. 16 shows a catheter device with a removable optical pressure wire.
Figure 17:
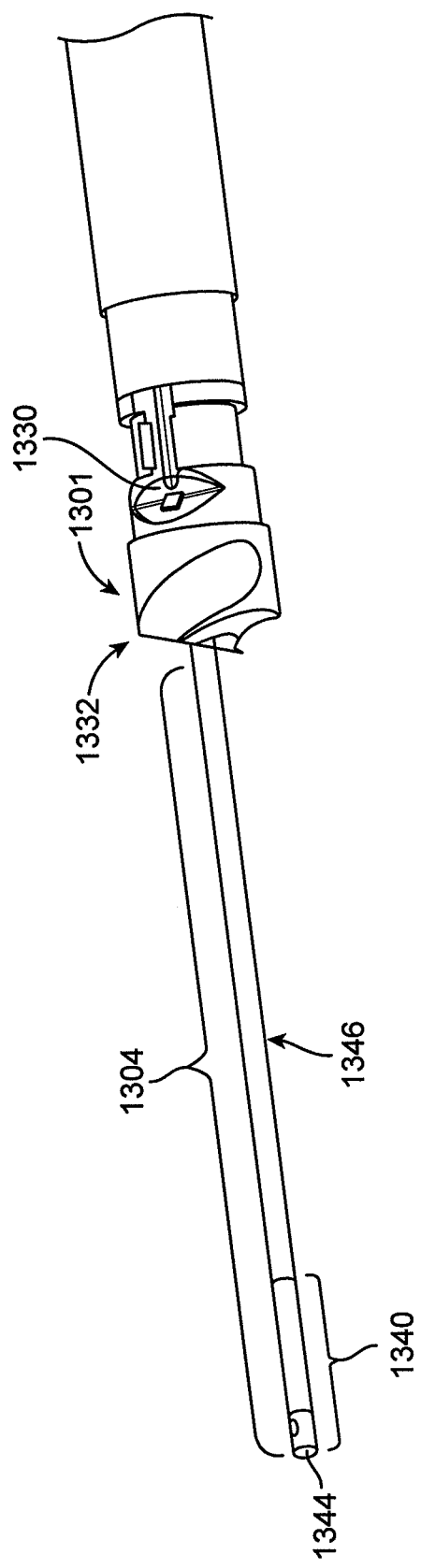
FIG. 17 shows the distal end of the catheter device in FIG. 16.
Figure 18:
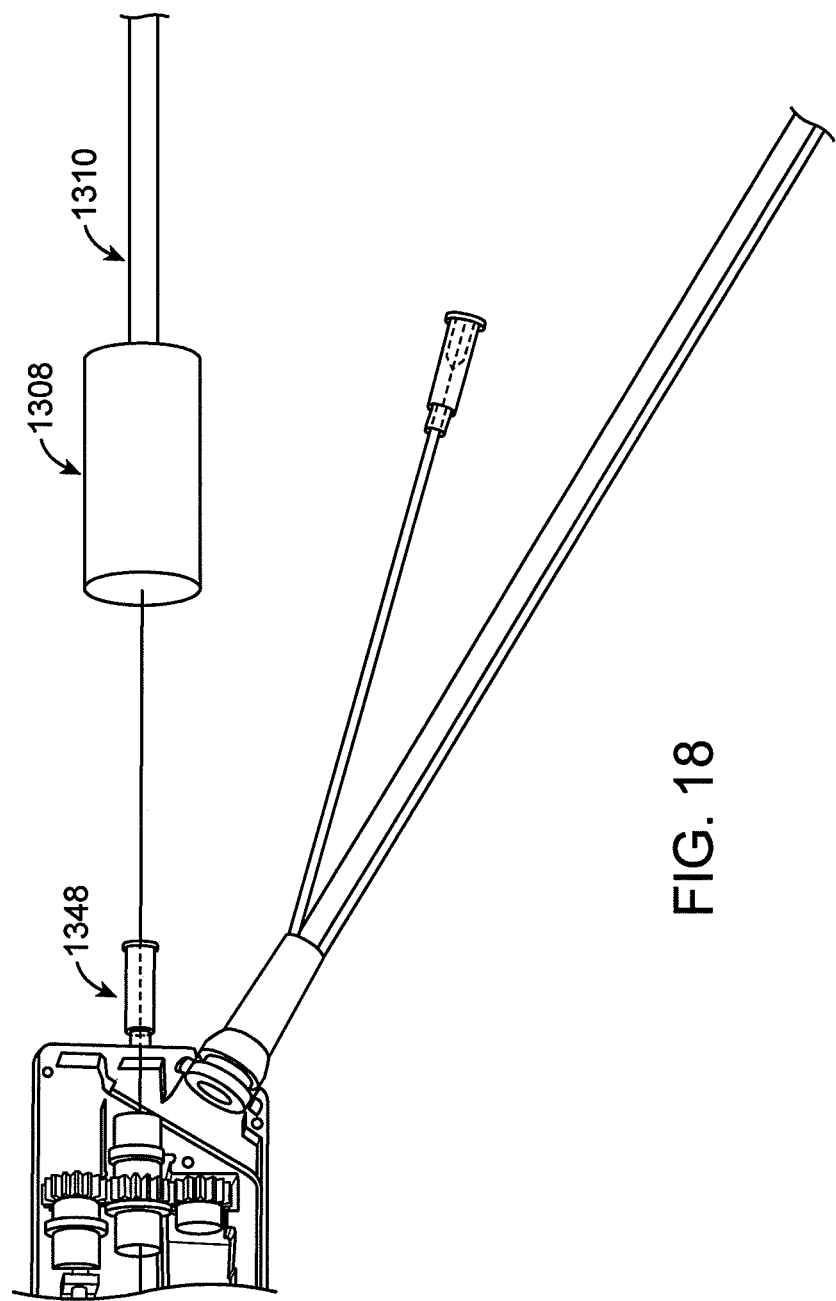
FIG. 18 shows the proximal end of the catheter device in FIG. 16 having an optical connector.

FIGS. 16-18 illustrate an example of this embodiment. Referring to FIGS. 16-18, an OCT imaging and occlusion-crossing device 1300 is shown. The device 1300 includes a catheter or flexible hollow shaft 1302 with a distal tip 1301. The distal tip 1301 includes an OCT imaging sensor 1330 and a cutter 1332 for removing an occlusion. The catheter 1302 includes a lumen extending from a proximal end through the distal tip 1301 of the catheter. The lumen allows the passage of a guide wire or the optical pressure sensor assembly 1304 through the catheter 1302. The optical pressure sensor assembly 1304 is dimensioned to pass through the existing lumen of the catheter 1302.

In operation, once the catheter 1302 is placed inside the patient's body using a guide wire the guide wire can be removed to insert the optical pressure sensor assembly 1304 through the catheter 1302. The pressure sensor assembly 1304 moves through the catheter tip 1301 to expose a sensing portion 1340 of the assembly 1304 to the surrounding intravascular environment. Alternatively, in some variations, the pressure sensor assembly 1304 also functions as a guide wire, in which case it eliminates the need for a separate guide wire.

As shown in FIGS. 16-18, the assembly 1304 includes an elongate hollow body 1346 with a distal portion 1304 having a hole covered by a deflectable membrane 1344. An optic fiber resides in the elongate hollow body 1346 with a distal firing end positioned near the membrane 1344. The distal firing end of the fiber is aligned and orientated such that emitted light can encounter the membrane 1344 and reflected/scattered light from the membrane can re-enter the fiber for detection by receiving electronics connected to the optical pressure sensor assembly. In some cases, the OCT console shown in FIG. 10 functions as receiving electronics to compute a pressure value based on the light received in the fiber from the membrane.

Additionally, the proximal end of the pressure sensor assembly 1348 may include a first optical connector for coupling to a second connector 1308. The second connector 1308 may be fused to another optic fiber in optical communication with a light source. The proximal end of the assembly may also connect to an OCT imaging console for pressure sensing.

Figure 23:
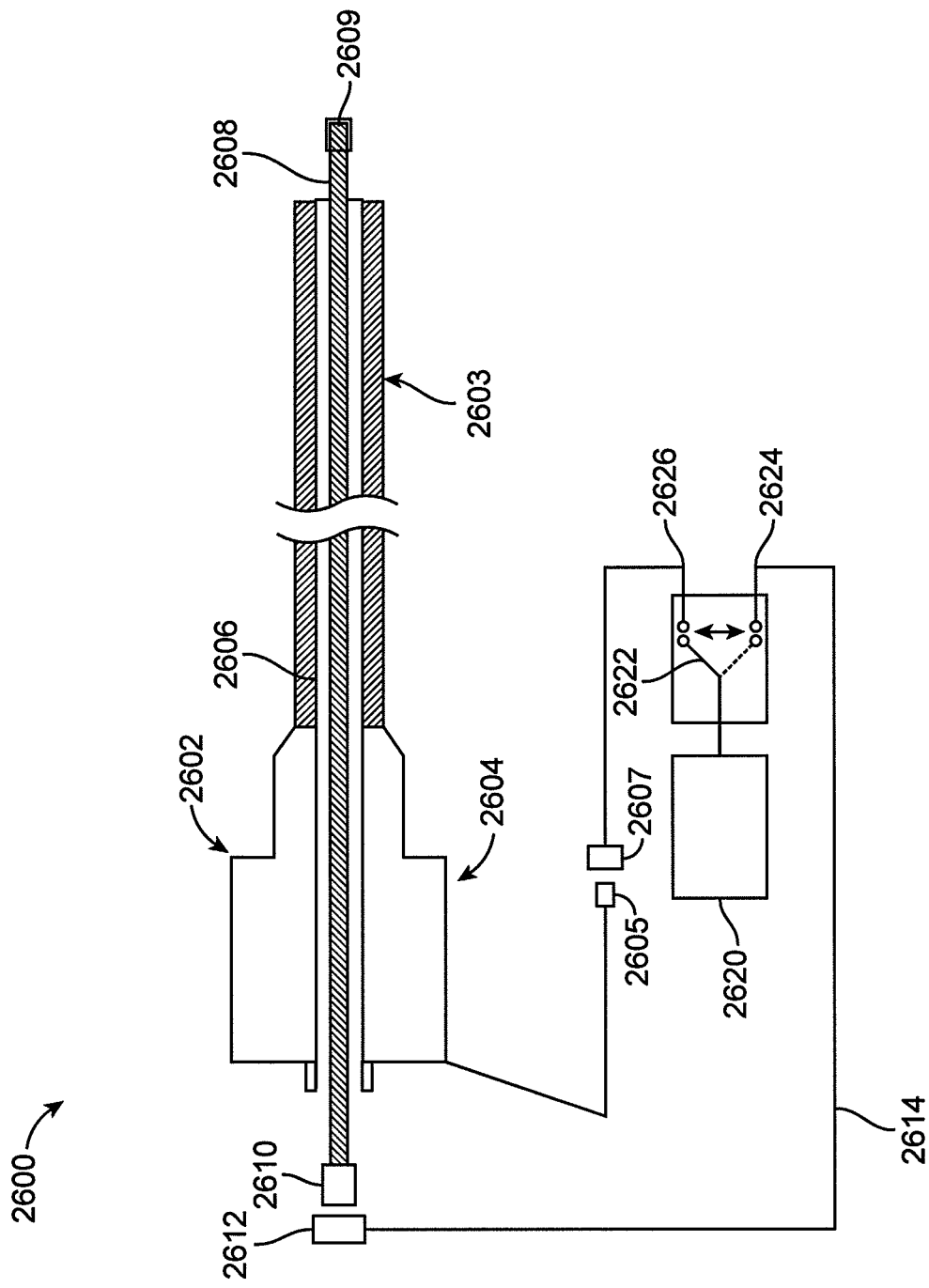
FIG. 23 schematically shows a pressure sensor assembly in use with an imaging system (e.g. OCT system).

FIG. 23 schematically illustrates an OCT system 2600 for use with an optical pressure sensor assembly 2608 that can be passed through a lumen of an intravascular device 2603. The OCT and pressure sensing system 2600 includes an OCT device 2602 having a hollow shaft 2606 defining an internal lumen. The OCT device 2602 includes an actuator or handle portion 2604 for controlling the device 2603. An optical pressure sensor assembly 2608 extends through the lumen of the device 2603 with a pressure sensing portion residing distal of the distal end of the device 2603.

The proximal end of the pressure sensor assembly includes an optical connector 2610 for coupling to a system connector 2612 that is in communication with a console 2620 via line 2614. In some embodiments, the console 2620 includes an optical switch 2622 for controlling the transmission of light between the OCT device and the optical pressure sensor assembly. In one mode, the optical switch 2622 connects the console 2620 (and light source) to the device 2603 via connectors 2605 and 2607. In another mode, the optical switch 2622 connects the console 2620 (and light source) to the pressure sensor assembly.

Referring again to FIG. 10, in another aspect, embodiments provided for an integrated intravascular device 312 having a built-in optical pressure sensing assembly. OCT/occlusion-crossing catheter 312 has (1) OCT imaging; (2) occlusion-crossing; and (3) pressure sensing features. The integrated intravascular device 312 has a catheter or elongate body with a central lumen extending therethrough. The catheter has a rotatable tip at the distal end of the catheter. The rotatable tip having an opening covered by a deflectable membrane. An optic fiber sits in the central lumen with a firing end near the opening. In some embodiments, the optic fiber is also configured to rotate with the rotatable tip.

In some variations, the catheter 312 can switch between imaging and pressure measurement modes. In one operation mode, the catheter 312 rotates and provides OCT images showing the vessel structure. In another mode, the catheter 312 does not rotate (e.g. relatively fixed rotationally) and measures the intravascular pressure. In some embodiments, the same optical fiber used for OCT imaging is used for pressure measurement.

Another example of a catheter with built-in pressure sensing features is an atherectomy catheter that includes an elastic membrane and fixed or removable optical pressure wire/fiber. The elastic membrane is movable in response to pressure. When a pressure reading is needed the catheter is connected to an imaging system that provides a light source, detector, and other receiving electronics to compute pressure based on optical properties of light scattered or reflected by the membrane.

Figure 19:
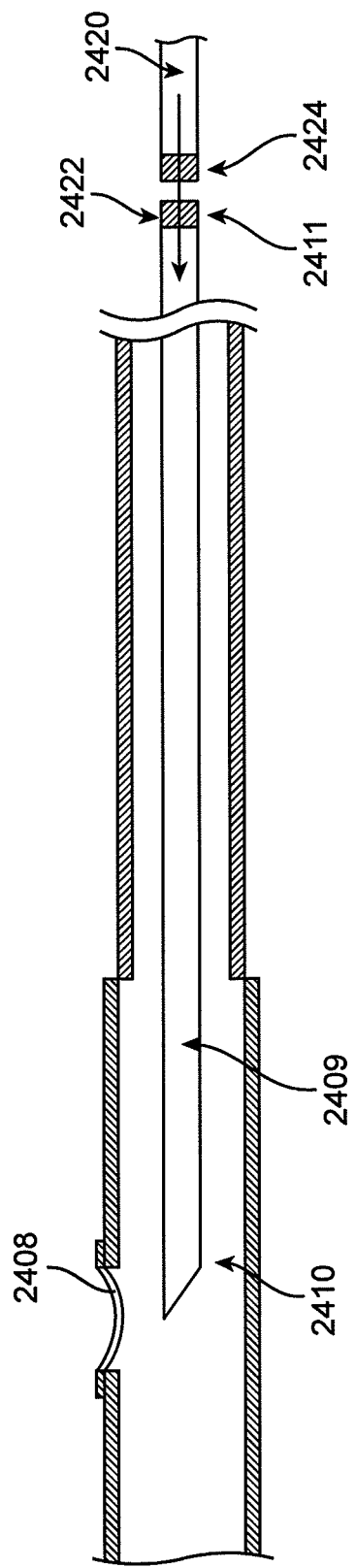
FIG. 19 is a cross-section view of a pressure wire assembly having an optical connector at the proximal end of the fiber.

For any of the described embodiments, any suitable optical connector may be used. As shown in FIG. 19, the proximal end 2411 of the fiber 2309 includes an optical connector adapted to couple the fiber to a light source. The light source is another optical fiber 2420 that is presumably connected to light source (e.g. laser). The source optical fiber 2420 includes an optical connector 2424 on a distal end for interfacing the optical connector 2422 of the receiving fiber 2410. Any suitable optical connectors may be used, including an element of similar diameter to a GRIN fiber for efficient coupling. Additionally, the proximal end 2411 of the fiber receiving 2410 may be cleaved (e.g. angle cleaved) and positioned to focus light from the source optical fiber 2420 into the receiving optical fiber 2410.

Figure 20:
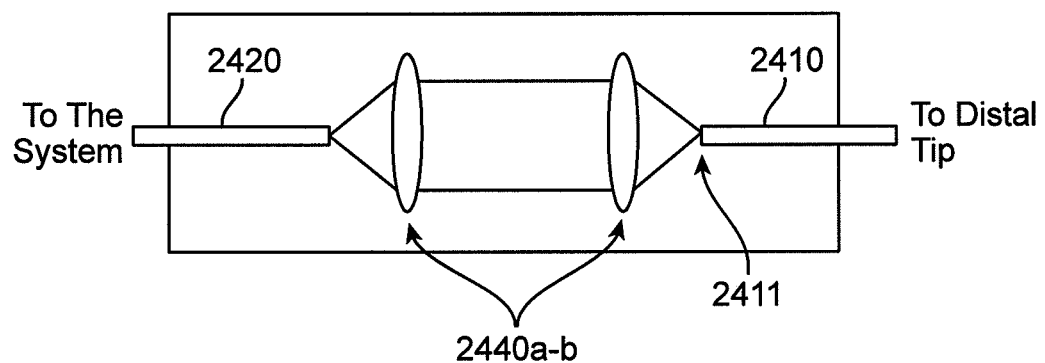
FIG. 20 is a schematic representation of exemplary optical connectors.
Figure 21:
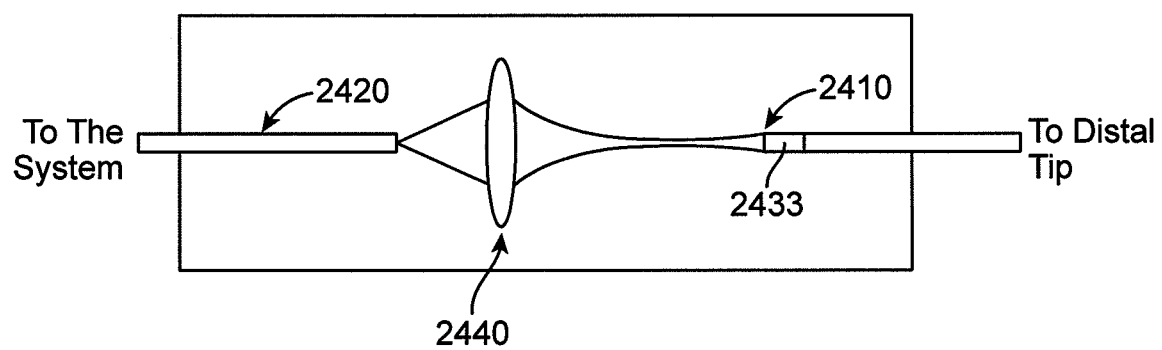
FIG. 21 is a schematic representation of alternative optical connectors.

FIGS. 20-21 show additional optical coupling variations. FIG. 20 shows a set of lenses 2440*a-b* for collimating light from a first optical fiber 2420 from the system to a second optical fiber 2410 in the pressure measuring catheter. FIG. 21 shows a similar coupling mechanism with a single lens 2440. A GRIN lens 2433 is also located at the coupling end of the second optical fiber configured for receiving/transmitting light to the first optical fiber.

III. Methods of Measuring Pressure with an Optical Pressure Sensor Assembly

Additional details describing the methods of measuring pressure with an optical pressure sensor assembly are provided in this section. As a general matter, any methods used for optical interferometry are applicable to detecting reflected and scattered light from a reference and a target. Typically, interferometers transmit light from a source through an optical fiber. The transmitted light is often split into two beams where a first beam is directed to a reference structure and a second beam is directed to a target structure. When each beam encounters a structure, the structure will reflect and/or scatter the received light. Some of the reflected/scattered light will enter the optical fiber and travel to a detector. The detector or a separate processor in communication with the detector can use the received light to determine the distance between the transmitting end of the optical fiber and the scatter/reflection point on the encountered structure.

As discussed above, this distance information can be used to compute intravascular pressure where distance is proportional to pressure. Optical pressure sensor assemblies include a movable membrane such as a deflectable membrane that varies in distances from the optical fiber depending on surrounding blood pressure. The movable membrane serves as the target structure from which transmitted light is reflected or scattered back into and received by the optical fiber. This reflected/scattered light is received and processed to determine the distance between the optical fiber and the deflected membrane.

Although distance can be measured in any suitable unit, in some embodiments, the distances are presented by an intensity vs. pixel depth relationship. As shown in FIGS. 7-8, the pixel depths corresponding to peak intensities indicate distances between the optical fiber and the movable membrane. When deflected, the distances between the membrane and the fiber decreases, which is indicated by a decrease in pixel depth. The change in this distance can be used to determine pressure. For example, a processor (or the detector) can calculate the change in $\Delta x$ distance between the peaks in FIG. 7 and FIG. 8. The change in distance is then compared to calibration data for the pressure sensor assembly. The calibration data can include the deflection distance to pressure relationship for the movable membrane (see FIG. 9).

Alternatively, intravascular pressure may computed by determining the amount of distance that a membrane has deflected in response to pressure exerted against the membrane. In such cases, the optical pressure sensor assembly may include a baseline distance $D_0$ indicating a first distance between the membrane and the fiber without deflection from pressure. The first distance is compared to a second distance $D_s$ where the second distance is a deflected distance for the membrane under pressure. Typically, the second distance will be closer to the optic fiber as the pressure is exerted against an outer surface of the membrane to depress the membrane toward the optic fiber. The difference ($\Delta y$) between the first and second distance can be computed and compared to a deflection-pressure rate or relationship for the assembly to determine the pressure exerted to deflect the membrane.

In order to determine the value of the second distance, optical interferometry can be used as described. This can include the steps of transmitting light from a source through an optical fiber, transmitting the light from the optical fiber to a deflected surface of an elastic membrane, and transmitting light reflected or scattered light from the elastic membrane to a detector or processor that can compute the second distance based on properties of the received light.

In some variations, as described, an interference signal is created from the interaction of a reference reflection signal and a membrane reflected/scattered signal. A processor or controller etc. may be used to determine the second distance of the deflected membrane from the properties of the interference signal.

Once the second distance is determined, the distance difference $\Delta y$ is calculated by subtracting $D_s$ from $D_0$. The distance difference is then compared to a predetermined deflection distance to pressure rate or relationship for the membrane and the pressure assembly. In some embodiments, a processor, detector, controller etc. is configured to compute or derive pressure from the membrane-to-fiber distance information.

Additionally, in other embodiments, pressure is determined without calculating a distance difference $\Delta y$. Rather, a single distance detected between the movable membrane and optical fiber is correlated to pressure.

Furthermore, pressure may be measured multiple times at multiple locations. For example, pressure may be measured prior to starting a procedure to confirm that the pressure gradient or pressure ratio (FFR) satisfies a threshold value warranting the procedure. Similarly, pressure may be measured after a procedure to confirm that a vessel has been adequately widened.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. An imaging and optical pressure sensor assembly, comprising:
    an optical fiber configured for optical communication with a light source;
    a housing comprising a lumen through which the optical fiber extends; and
    an elastic membrane positioned across an opening in a sidewall of the housing and attached to the housing at both sides of the opening, the elastic membrane configured to be movable relative to the housing in response to a pressure outside of the housing, the elastic membrane further configured to reflect or scatter light from the optical fiber;
    wherein a distal end of the optical fiber is configured to transmit light from the light source to the elastic membrane and to receive the light reflected or scattered by the elastic membrane and wherein the optical fiber is configured to rotate and the distal end of the optical fiber is configured to transmit light from the light source through the opening to tissue and to receive light reflected or scattered by the tissue as the optical fiber rotates;
    an interface medium at the distal end of the optical fiber, the interface medium configured to produce a reference reflection when the light is transmitted from the light source through the optical fiber to the elastic membrane or the tissue; and a controller configured to:
determine the pressure outside of the housing based upon the light reflected or scattered by the elastic membrane and the reference reflection; and
generate an image of the tissue based upon the light reflected or scatted by the tissue and the reference reflection.

2. The assembly of claim 1, wherein the optical fiber is moveable relative to the housing.

3. The assembly of claim 1, wherein the elastic membrane is adapted to deflect toward the optical fiber under positive pressure.

4. The assembly of claim 1, wherein the elastic membrane comprises a convex surface facing the optical fiber when the elastic membrane is deflected under positive pressure.

5. The assembly of claim 1, wherein the elastic membrane is configured to cover the opening.

6. The assembly of claim 1, wherein the elastic membrane is made from fluorinated ethylene propylene.

7. The assembly of claim 1, wherein the elastic membrane comprises a first surface facing the optical fiber and a second surface configured to face an intravascular lumen, the distance between the first surface and the optical fiber decreasing when positive pressure is applied to the second surface of the elastic membrane.

8. The assembly of claim 1, wherein the elastic membrane is adapted to move toward a central longitudinal axis of the housing under positive pressure.

9. The assembly of claim 1, further comprising a memory storage device storing pressure sensor calibration data.

10. The assembly of claim 9, wherein the calibration data comprises a pressure to deflection relationship for the elastic membrane.

11. The assembly of claim 1, further comprising an Electrically Erasable Programmable Read-Only Memory (EEPROM) storing pressure sensor calibration data for the assembly.

12. The assembly of claim 1, further comprising a mirror aligned with the opening to reflect light exiting the optical fiber toward the elastic membrane.

13. The assembly of claim 1, wherein the interface medium has a first refractive index different from a second refractive index of the optical fiber, wherein the differing refractive indices creates the reference reflection.

14. The assembly of claim 13, wherein the interface medium is an adhesive.

15. The assembly of claim 1, further comprising a lens configured to transmit collimated light into a proximal end of the optical fiber.

16. The assembly of claim 1, wherein the assembly is dimensioned for insertion through an intravascular catheter lumen.

17. The assembly of claim 1, wherein the optical fiber is axially slidable relative to the housing.

18. A method of imaging and determining pressure in a blood vessel comprising:
transmitting light from a light source through an optical fiber in a housing through an interface medium to a surface of an elastic membrane, wherein the elastic membrane is attached to the housing and positioned across an opening in a sidewall of the housing, the elastic membrane moveable in response to pressure exerted against the elastic membrane;
transmitting reflected or scattered light from the elastic membrane and the interface medium back through the optical fiber;
generating an intravascular pressure measurement based upon the light transmitted backthrough the optical fiber from the elastic membrane and the interface medium;
rotating the optical fiber;
transmitting light from the light source through the optical fiber to tissue of the blood vessel through the interface medium and the opening as the optical fiber rotates;
transmitting reflected or scattered light from the tissue and the interface medium backth rough the optical fiber as the optical fiber rotates; and
generating optical coherence tomography images of the blood vessel I based upon the light transmitted back through the optical fiber from the tissue and the interface medium.

19. The method of claim 18, wherein the generating an intravascular pressure measurement step comprises computing the intravascular pressure measurement based on a membrane deflection distance between a surface of the elastic membrane and the optical fiber.

20. The method of claim 19, wherein the membrane deflection distance is indicated by an intensity value and a depth value for the light transmitted back through the optical fiber from the elastic membrane.

21. The method of claim 18, wherein the generating an intravascular pressure measurement step comprises transmitting data from a detector to a processor, wherein the data represents an interference signal resulting from the interaction of the light transmitted back through the optical fiber from the interface medium and the light transmitted back through the optical fiber from the elastic membrane the processor computing the intravascular pressure based on the interference signal.

22. The method of claim 18, wherein the generating an intravascular pressure measurement step comprises computing a path length from the optical fiber and the deflected surface of the membrane, the computation based on a difference in phase, time or frequency between the light transmitted back through the optical fiber from the interface medium and the light transmitted back through the optical fiber from the elastic membrane.

23. The method of claim 18 further comprising calculating a fractional flow reserve for the blood vessel.

24. The method of claim 18 further comprising calculating a first pressure at a first location and a second pressure at a second location.

* * * * *